(12) United States Patent
Youngs et al.

(10) Patent No.: US 11,197,873 B2
(45) Date of Patent: Dec. 14, 2021

(54) AZOLIUM SALTS FOR TREATMENT OF NON-MUSCLE INVASIVE BLADDER CANCER

(71) Applicants: The University of Akron, Akron, OH (US); The Institute for Cancer Research, Philadelphia, PA (US)

(72) Inventors: Wiley Jay Youngs, Akron, OH (US); Philip H. Abbosh, Hatboro, PA (US); Michael Lee Stromyer, Allison Park, PA (US); Marie Renee Southerland, Ravenna, OH (US); Uttam Satyal, Philadelphia, PA (US); David Joseph Weader, Harrisburg, PA (US)

(73) Assignees: The University of Akron, Akron, OH (US); The Institute for Cancer Research, Philadelphia, PA (US)

( * ) Notice: Subject to any disclaimer, the term of this patent is extended or adjusted under 35 U.S.C. 154(b) by 0 days.

(21) Appl. No.: 16/891,607

(22) Filed: Jun. 3, 2020

(65) Prior Publication Data
US 2020/0376009 A1     Dec. 3, 2020

Related U.S. Application Data

(60) Provisional application No. 62/856,330, filed on Jun. 3, 2019.

(51) Int. Cl.
*A61K 31/675* (2006.01)
*A61K 31/423* (2006.01)
*A61K 49/00* (2006.01)

(52) U.S. Cl.
CPC .......... *A61K 31/675* (2013.01); *A61K 31/423* (2013.01); *A61K 49/006* (2013.01)

(58) Field of Classification Search
CPC .................................................. A61K 31/675
See application file for complete search history.

(56) References Cited

U.S. PATENT DOCUMENTS

2014/0142307 A1\* 5/2014 Youngs ................ C07D 235/02
544/273

\* cited by examiner

*Primary Examiner* — Alicia L Otton
(74) *Attorney, Agent, or Firm* — Renner, Kenner, Greive, Bobak, Taylor & Weber

(57) ABSTRACT

The present invention provides pharmaceutical compounds for the treatment of high-grade superficial bladder cancer in patent in need thereof. Further described are compositions of azolium salts for use in such treatment.

2 Claims, 15 Drawing Sheets
(8 of 15 Drawing Sheet(s) Filed in Color)

AZOLIUM SALTS FOR TREATMENT OF NON-MUSCLE INVASIVE BLADDER CANCER

FIELD OF THE INVENTION

This invention relates to pharmaceutical compounds for the treatment of bladder cancer. Specifically, this invention pertains to azolium salts.

BACKGROUND OF THE INVENTION

Bladder cancer will be diagnosed in the United States in 80,000 patients in 2019, with about ⅓ of these patients harboring high-grade superficial cancer. Management of high-grade superficial bladder cancer is significantly more challenging for these patients now that Bacillus Calmette Guerin (BCG), the long-time standard-of-care, is in short supply due to the manufacturing discontinuation by Sanofi and difficulty in manufacturing and QC by Astellas, the main producers. With this shortage, 40 years of successful treatment of bladder cancer has been reversed. There have been multiple yearlong shortages in the last 5 years and the situation is not expected to improve.

Second-line therapies, such as intravesical gemcitabine, valrubicin, and docetaxel, predictably have little chance of success because they only act at specific points in the cell cycle and cannot practically be retained in the bladder long enough to have an effect. Clinical experience with these approaches in BCG-failure patients results in 70-80% failure rate and often radical cystectomy (removal of the bladder). Radical cystectomy is among the most complicated and expensive elective surgeries performed. In addition, radical cystectomy requires permanent urinary diversion, typically with a urostomy, which is life-altering. Avoidance of radical cystectomy is therefore likely a high priority for patients and this is reflected in medical literature and new clinical trials. Although effective, high grade superficial bladder cancer progresses to metastasis or death in about ⅓ of cases even with BCG. BCG really only reduces the risk of cancer progression (i.e. reduces the need for radical cystectomy) by 27%. One redeeming quality of the currently-available treatments for high-grade superficial bladder cancer is the use of intravesical administration. Systemic absorption and symptoms associated with intravesical administration are greatly reduced compared to parenteral or oral administration. However, BCG can still cause systemic symptoms such as fever, malaise, and rarely sepsis, and also local symptoms such as urinary urgency/frequency/dysuria by virtue of its nature as a live bacterial immunogenic vaccine. It is clear there is an urgent and genuine need for better intravesical chemotherapeutics to help circumvent the BCG shortage, its relative ineffectiveness, and the inadequacies of second line therapies.

SUMMARY OF THE INVENTION

An embodiment of the present invention provides A pharmaceutical composition of an antineoplastic triphenylphosphonium-substituted azolium salt for the effective treatment of human bladder cancers comprising:

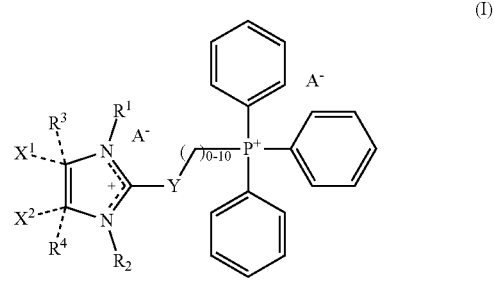

(I)

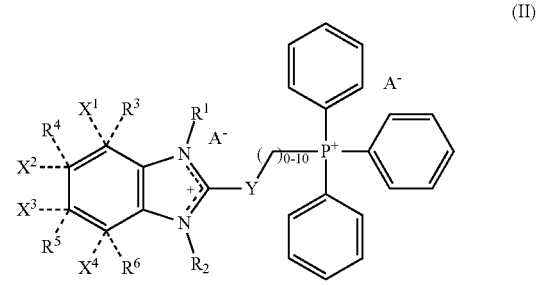

(II)

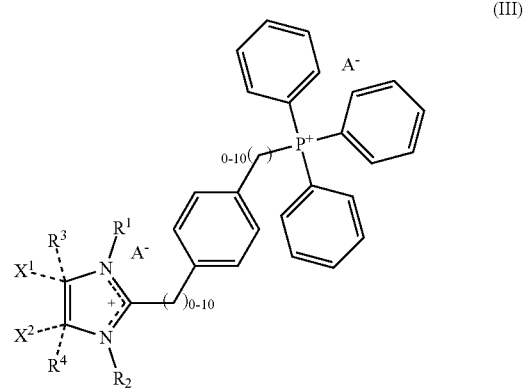

(III)

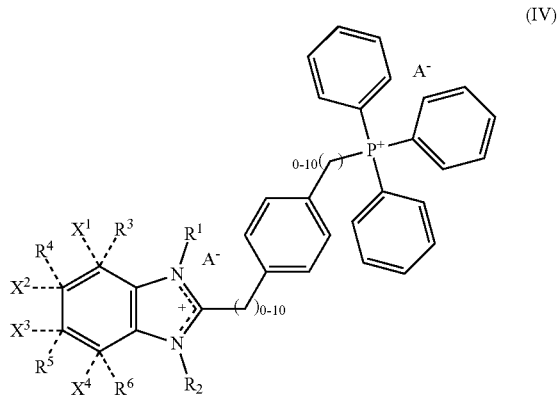

(IV)

-continued

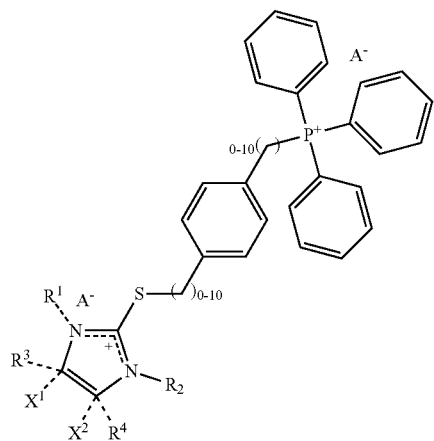
(V)

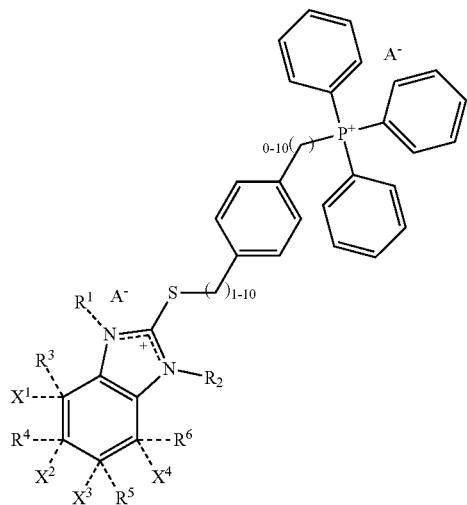
(VI)

wherein, the dashed lines in the structures (I)-(VI) represent the attachment of either R or X to the corresponding ring atom; wherein, X is defined as a halogen selected from F, Cl, Br, or I, and where all X groups may be the same halogen or chosen independently at each position; wherein, R1 and R2 are each independently selected from: hydrogen; C1 to C20 alkyl; C1 to C20 substituted alkyl; C1 to C20 alkyl heteroatom groups where the heterotatom is selected from S, O, or N; C3 to C12 cycloalkyl; C3 to C12 substituted cycloalkyl; C2 to C12 alkenyl; C3 to C12 cycloalkenyl; C3 to C12 substituted cycloalkenyl; C2 to C12 alkynyl; C6 to C12 aryl; C5 to C12 substituted aryl; polycyclic aromatics, substituted polycyclic aromatics; C6 to C12 arylalkyl; C6 to C12 alkylaryl; C3 to C12 heterocyclic; C3 to C12 substituted heterocyclic; C1 to C12 alkoxy; C1 to C12 alcohols; C1 to C12 carboxy; biphenyl; C1 to C6 alkyl biphenyl; C2 to C6 alkenyl biphenyl; or C2 to C6 alkynyl biphenyl, chemotherapy compounds or derivatives thereof; tumor suppressor compounds or derivatives thereof; wherein, R3, R4, R5, and R6, if present, are each independently selected from: hydrogen; C1 to C20 alkyl; C1 to C20 substituted alkyl; C1 to C20 alkyl heteroatom groups where the heterotatom is selected from S, O, or N; C3 to C12 cycloalkyl; C3 to C12 substituted cycloalkyl; C2 to C12 alkenyl; C3 to C12 cycloalkenyl; C3 to C12 substituted cycloalkenyl; C2 to C12 alkynyl; C6 to C12 aryl; C5 to C12 substituted aryl; polycyclic aromatics, substituted polycyclic aromatics; C6 to C12 arylalkyl; C6 to C12 alkylaryl; C3 to C12 heterocyclic; C3 to C12 substituted heterocyclic; C1 to C12 alkoxy; C1 to C12 alcohols; C1 to C12 carboxy; biphenyl; C1 to C6 alkyl biphenyl; C2 to C6 alkenyl biphenyl; or C2 to C6 alkynyl biphenyl; hydroxyl; carbonyl; amino; acetyl; acetoxy; oxo; nitro; cyano; isocyano; cyanato; isocyanato; chemotherapy compounds or derivatives thereof; tumor suppressor compounds or derivatives thereof; wherein, one or more of the ring carbon atoms to which R3, R4, R5, R6 and R7 are attached can be replaced by a nitrogen, oxygen or sulfur atom; wherein, A- is defined as an anion independently selected as a halide, hydroxide, alkoxide, aryloxide, carboxylate, sulfate, phosphate, triflate, tosylate, nitrite, or borate; wherein, Y is defined as a carbon or sulfur atom.

Another embodiment of the present invention provides a pharmaceutical composition of an antineoplastic triphenylphosphonium-substituted azolium salt for the effective treatment of human bladder cancers comprising:

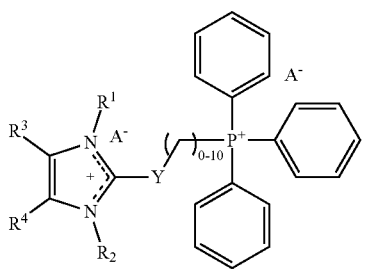
(I)

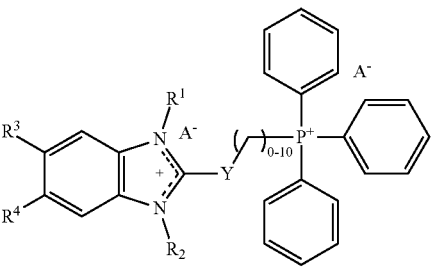
(II)

wherein, R1 and R2 are naphthalen-2-ylmethyl; wherein, R3 and R4, if present, are each independently selected from: hydrogen; C1 to C10 alkyl; C1 to C10 substituted alkyl; C1 to C10 alkyl heteroatom groups where the heteroatom is selected from S, O, or N; C3 to C12 cycloalkyl; C3 to C12 substituted cycloalkyl; C2 to C12 alkenyl; C3 to C12 cycloalkenyl; C3 to C12 substituted cycloalkenyl; C2 to C12 alkynyl; C6 to C12 aryl; C5 to C12 substituted aryl; polycyclic aromatics, substituted polycyclic aromatics; C6 to C12 arylalkyl; C6 to C12 alkylaryl; C3 to C12 heterocyclic; C3 to C12 substituted heterocyclic; C1 to C12 alkoxy; biphenyl; C1 to C6 alkyl biphenyl; C2 to C6 alkenyl biphenyl; or C2 to C6 alkynyl biphenyl; wherein, A- is defined as an anion independently selected as a halide, carboxylate, sulfate, phosphate, triflate, tosylate, nitrite, or borate; wherein, Y is defined as a carbon or sulfur atom.

Another embodiment of the present invention provides a select methine cyanine dye imidazolium salt for the effective treatment and imaging of human bladder cancer comprising:

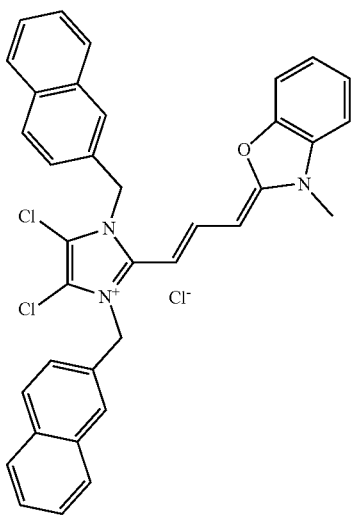

(III)

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF ILLUSTRATIVE EMBODIMENTS

Figure 1:
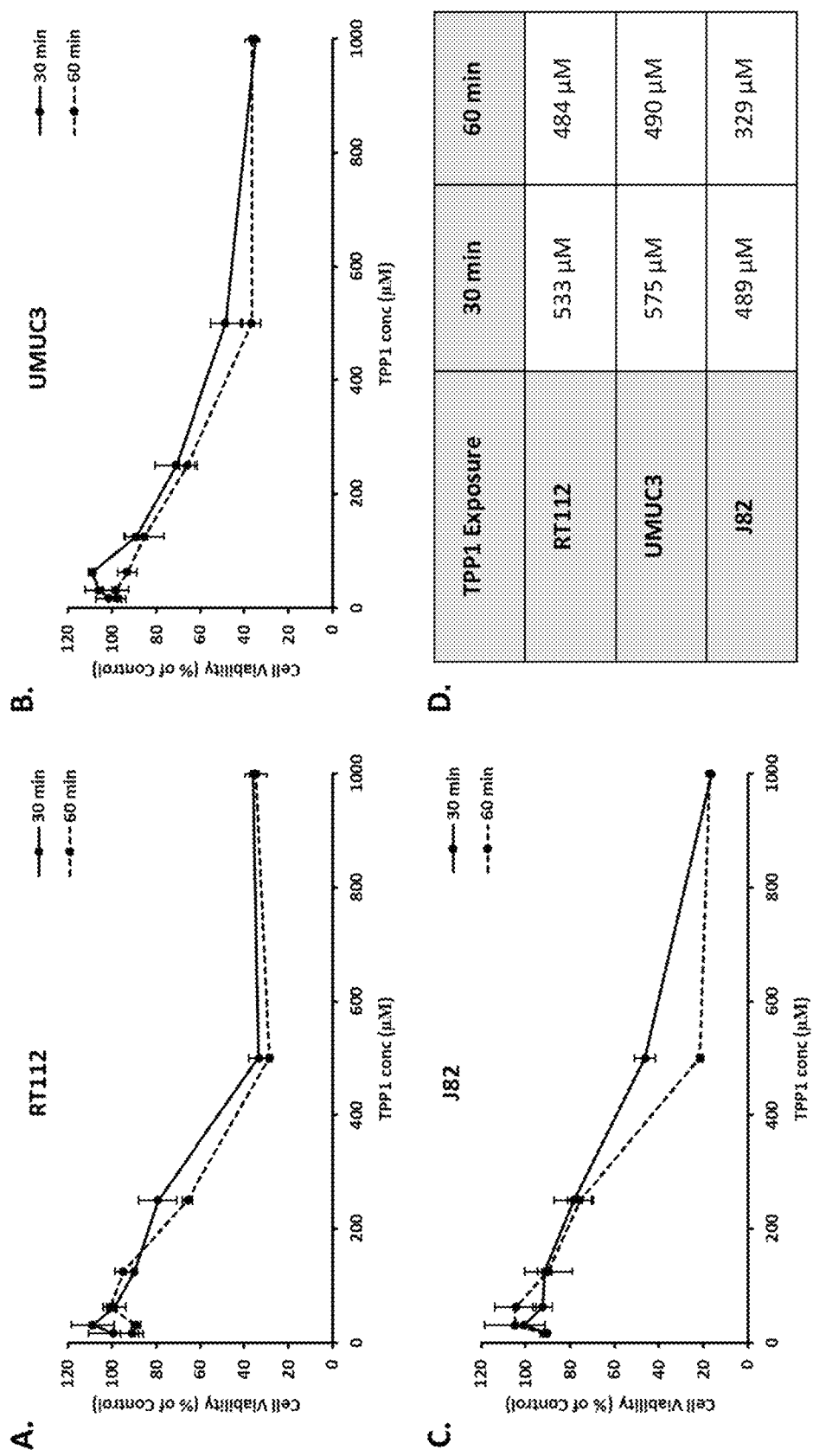
FIG. 1 provides growth inhibition of an imidiazolium compound of this invention as assessed at various concentrations against different bladder cancer cell lines at 30 min and 1 h exposure times, with growth inhibition to RT112 shown in part A., to UMUC3 shown in part B., and to J82 shown in part C. The estimated GI50 values for each cell line showed exposure-time dependent cytotoxicity in part D.

In various aspects, the present invention provides imidazolium salts as a class of chemical compounds that possess potent antineoplastic activity toward bladder cancer. Current treatments for superficial bladder cancer include intravesical BCG and chemotherapy. Intravesical imidazolium salts have several favorable characteristic compared to existing therapies including ease of manufacture, apparent mechanism of action, short duration of exposure with maximum cytotoxicity, and potentially the ability to induce a significant effect on bladder cancer with less treatments (one to two) than current standards (six).

In a first aspect, the present invention is directed to novel triphenylphosphonium substituted imidazolium salts according to the formulas:

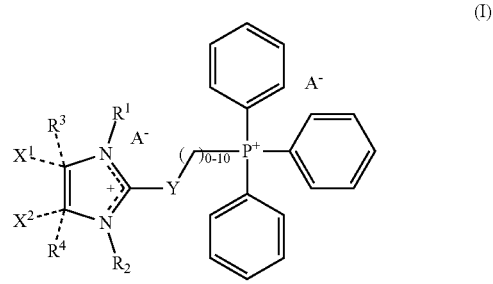

(I)

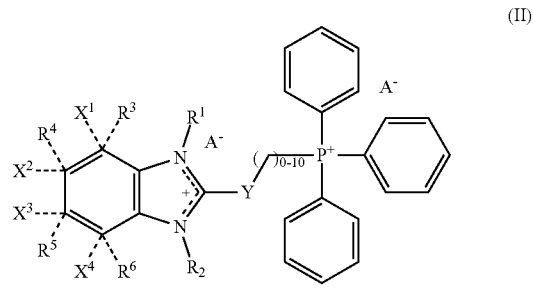

(II)

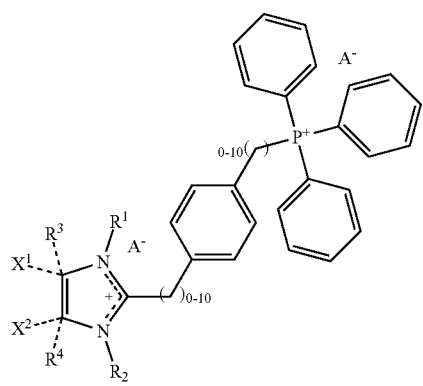

(III)

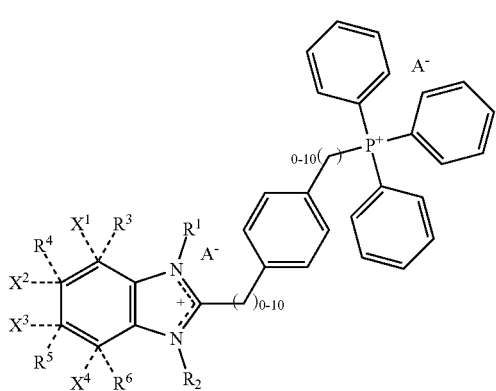

(IV)

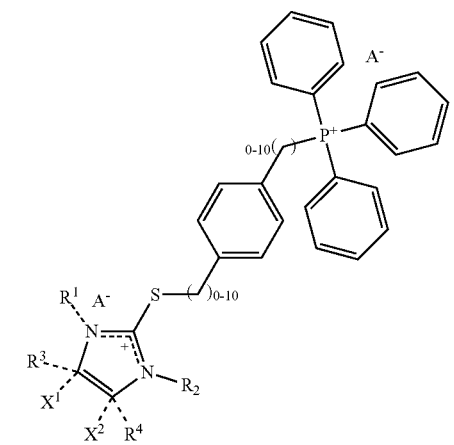

(V)

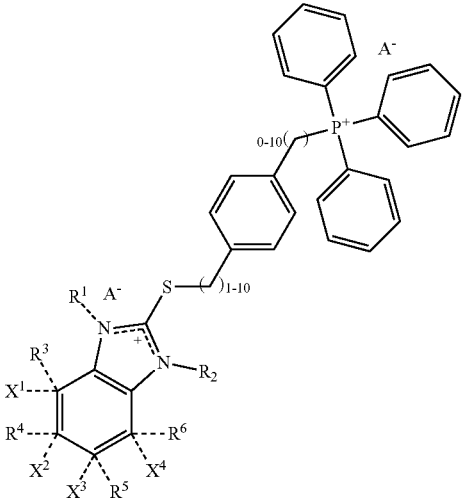

(VI)

In various embodiments, the dashed lines in the structures represent the variable attachment of either R or X to its corresponding ring atom.

In various embodiments, X is defined as a halogen (F, Cl, Br, or I) and where all X groups present may be the same halogen or chosen independently at each position.

In various embodiments, $R^1$ and $R^2$ are each independently selected from hydrogen; C1 to C20 alkyl; C1 to C20 substituted alkyl; C1 to C20 alkyl heteroatom groups where the heterotatom is selected from S, O, or N; C3 to C12 cycloalkyl; C3 to C12 substituted cycloalkyl; C2 to C12 alkenyl; C3 to C12 cycloalkenyl; C3 to C12 substituted cycloalkenyl; C2 to C12 alkynyl; C6 to C12 aryl; C5 to C12 substituted aryl; polycyclic aromatics, substituted polycyclic aromatics; C6 to C12 arylalkyl; C6 to C12 alkylaryl; C3 to C12 heterocyclic; C3 to C12 substituted heterocyclic; C1 to C12 alkoxy; C1 to C12 alcohols; C1 to C12 carboxy; biphenyl; C1 to C6 alkyl biphenyl; C2 to C6 alkenyl biphenyl; or C2 to C6 alkynyl biphenyl, chemotherapy compounds or derivatives thereof; tumor suppressor compounds or derivatives thereof.

In various embodiments, $R^3$, $R^4$, $R^5$, and $R^6$, if present, are each independently selected from hydrogen; C1 to C20 alkyl; C1 to C20 substituted alkyl; C1 to C20 alkyl heteroatom groups where the heterotatom is selected from S, O, or N; C3 to C12 cycloalkyl; C3 to C12 substituted cycloalkyl; C2 to C12 alkenyl; C3 to C12 cycloalkenyl; C3 to C12 substituted cycloalkenyl; C2 to C12 alkynyl; C6 to C12 aryl; C5 to C12 substituted aryl; polycyclic aromatics, substituted polycyclic aromatics; C6 to C12 arylalkyl; C6 to C12 alkylaryl; C3 to C12 heterocyclic; C3 to C12 substituted heterocyclic; C1 to C12 alkoxy; C1 to C12 alcohols; C1 to C12 carboxy; biphenyl; C1 to C6 alkyl biphenyl; C2 to C6 alkenyl biphenyl; or C2 to C6 alkynyl biphenyl; hydroxyl; carbonyl; amino; acetyl; acetoxy; oxo; nitro; cyano; isocyano; cyanato; isocyanato; chemotherapy compounds or derivatives thereof; tumor suppressor compounds or derivatives thereof.

In various embodiments, one or more of the ring carbon atoms to which $R^3$, $R^4$, $R^5$, $R^6$ and $R^7$ are attached can be replaced by a nitrogen, oxygen or sulfur atom. A– is defined as an anion independently selected as a halide, hydroxide, alkoxide, aryloxide, carboxylate, sulfate, phosphate, triflate, tosylate, nitrite, or borate. Y is defined as a carbon or sulfur atom.

In a second aspect, the present invention is directed to novel methine cyanine dye imidazolium salts according to the formula:

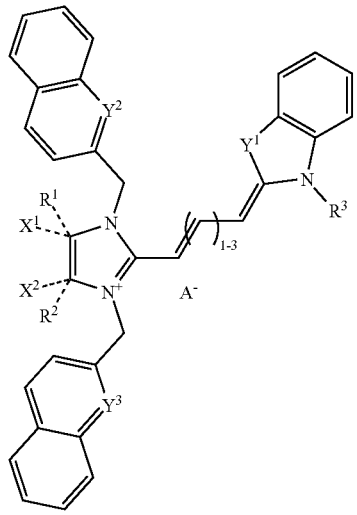

(V)

In various embodiments, the dashed lines in the structures represent the variable attachment of either R or X to its corresponding ring atom.

In various embodiments, X is defined as a halogen (F, Cl, Br, or I) and where all X groups present may be the same halogen or chosen independently at each position.

In various embodiments, $R^1$, $R^2$, and $R^3$ are each independently selected from hydrogen; C1 to C20 alkyl; C1 to C20 substituted alkyl; C1 to C20 alkyl heteroatom groups where the heterotatom is selected from S, O, or N; C3 to C12 cycloalkyl; C3 to C12 substituted cycloalkyl; C2 to C12 alkenyl; C3 to C12 cycloalkenyl; C3 to C12 substituted cycloalkenyl; C2 to C12 alkynyl; C6 to C12 aryl; C5 to C12 substituted aryl; polycyclic aromatics, substituted polycyclic aromatics; C6 to C12 arylalkyl; C6 to C12 alkylaryl; C3 to C12 heterocyclic; C3 to C12 substituted heterocyclic; C1 to C12 alkoxy; C1 to C12 alcohols; C1 to C12 carboxy; biphenyl; C1 to C6 alkyl biphenyl; C2 to C6 alkenyl biphenyl; or C2 to C6 alkynyl biphenyl, chemotherapy compounds or derivatives thereof; tumor suppressor compounds or derivatives thereof.

In various embodiments, $Y^1$ is defined as a heteroatom or substituent which may be selected from N, O, S, $NR^3$, or $R^3$. $Y^2$, and $Y^3$ are each independently selected from carbon or nitrogen.

In various embodiments, A– is defined as an anion independently selected as a halide, hydroxide, alkoxide, aryloxide, carboxylate, sulfate, phosphate, triflate, tosylate, nitrite, or borate.

In a third aspect, the present invention is directed to novel imidazolium salt as an effective treatment for bladder cancer according to the structure:

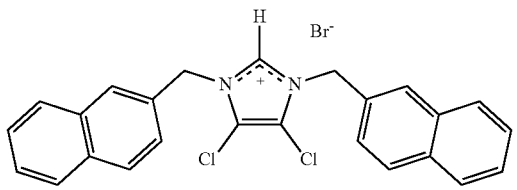

(VI)

In a fourth aspect, the present invention is directed to novel imidazolium salts that exhibit significant antineoplastic activity according to the structures:

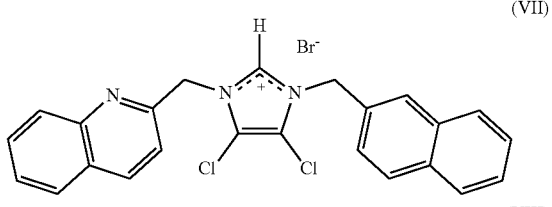

(VII)

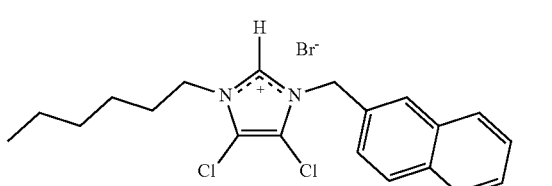

(VIII)

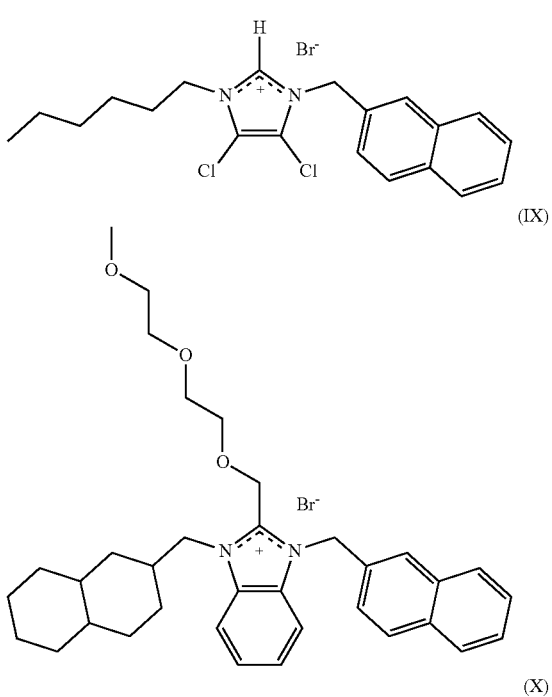

(IX)

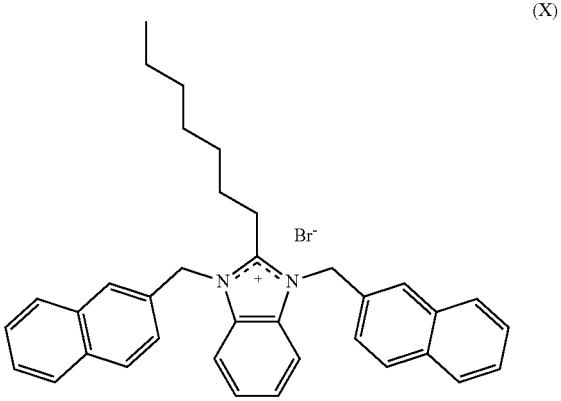

(X)

-continued

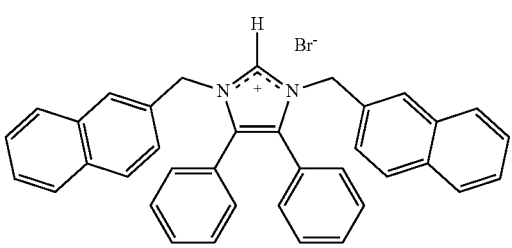
(XI)

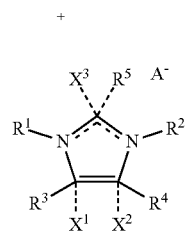
(XII)

In various embodiments, the dashed lines in the structures represent the variable attachment of either R or X to its corresponding ring atom.

In various embodiments, X is defined as a halogen (F, Cl, Br, or I) and where all X groups present may be the same halogen or chosen independently at each position.

In various embodiments, $R^1$ and $R^2$ are each independently selected from hydrogen; C1 to C20 alkyl; C1 to C20 substituted alkyl; C1 to C20 alkyl heteroatom groups where the heterotatom is selected from S, O, or N; C3 to C12 cycloalkyl; C3 to C12 substituted cycloalkyl; C2 to C12 alkenyl; C3 to C12 cycloalkenyl; C3 to C12 substituted cycloalkenyl; C2 to C12 alkynyl; C6 to C12 aryl; C5 to C12 substituted aryl; polycyclic aromatics, substituted polycyclic aromatics; C6 to C12 arylalkyl; C6 to C12 alkylaryl; C3 to C12 heterocyclic; C3 to C12 substituted heterocyclic; C1 to C12 alkoxy; C1 to C12 alcohols; C1 to C12 carboxy; biphenyl; C1 to C6 alkyl biphenyl; C2 to C6 alkenyl biphenyl; or C2 to C6 alkynyl biphenyl, chemotherapy compounds or derivatives thereof; tumor suppressor compounds or derivatives thereof.

In various embodiments $R^3$, $R^4$, $R^5$, and $R^6$, if present, are each independently selected from hydrogen; C1 to C20 alkyl; C1 to C20 substituted alkyl; C1 to C20 alkyl heteroatom groups where the heterotatom is selected from S, O, or N; C3 to C12 cycloalkyl; C3 to C12 substituted cycloalkyl; C2 to C12 alkenyl; C3 to C12 cycloalkenyl; C3 to C12 substituted cycloalkenyl; C2 to C12 alkynyl; C6 to C12 aryl; C5 to C12 substituted aryl; polycyclic aromatics, substituted polycyclic aromatics; C6 to C12 arylalkyl; C6 to C12 alkylaryl; C3 to C12 heterocyclic; C3 to C12 substituted heterocyclic; C1 to C12 alkoxy; C1 to C12 alcohols; C1 to C12 carboxy; biphenyl; C1 to C6 alkyl biphenyl; C2 to C6 alkenyl biphenyl; or C2 to C6 alkynyl biphenyl; hydroxyl; carbonyl; amino; acetyl; acetoxy; oxo; nitro; cyano; isocyano; cyanato; isocyanato; chemotherapy compounds or derivatives thereof; tumor suppressor compounds or derivatives thereof.

In various embodiments, one or more of the ring carbon atoms to which $R^3$, $R^4$, $R^5$, $R^6$ and $R^7$ are attached can be replaced by a nitrogen, oxygen or sulfur atom.

In various embodiments, A− is defined as an anion independently selected as a halide, hydroxide, alkoxide, aryloxide, carboxylate, sulfate, phosphate, triflate, tosylate, nitrite, or borate.

In a fifth aspect, the present invention is directed to novel S-substituted (alkylthio) imidazolium salts according to the formulas:

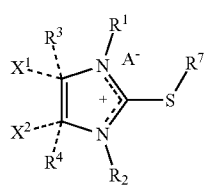
(I)

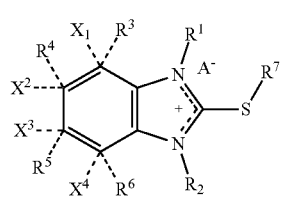
(II)

In various embodiments, the dashed lines in the structures represent the variable attachment of either R or X to its corresponding ring atom.

In various embodiments, X is defined as a halogen (F, Cl, Br, or I) and where all X groups present may be the same halogen or chosen independently at each position.

In various embodiments, $R^1$ and $R^2$ are each independently selected from hydrogen; C1 to C20 alkyl; C1 to C20 substituted alkyl; C1 to C20 alkyl heteroatom groups where the heterotatom is selected from S, O, or N; C3 to C12 cycloalkyl; C3 to C12 substituted cycloalkyl; C2 to C12 alkenyl; C3 to C12 cycloalkenyl; C3 to C12 substituted cycloalkenyl; C2 to C12 alkynyl; C6 to C12 aryl; C5 to C12 substituted aryl; polycyclic aromatics, substituted polycyclic aromatics; C6 to C12 arylalkyl; C6 to C12 alkylaryl; C3 to C12 heterocyclic; C3 to C12 substituted heterocyclic; C1 to C12 alkoxy; C1 to C12 alcohols; C1 to C12 carboxy; biphenyl; C1 to C6 alkyl biphenyl; C2 to C6 alkenyl biphenyl; or C2 to C6 alkynyl biphenyl, chemotherapy compounds or derivatives thereof; tumor suppressor compounds or derivatives thereof.

In various embodiments, $R^3$, $R^4$, $R^5$, and $R^6$, if present, are each independently selected from hydrogen; C1 to C20 alkyl; C1 to C20 substituted alkyl; C1 to C20 alkyl heteroatom groups where the heterotatom is selected from S, O, or N; C3 to C12 cycloalkyl; C3 to C12 substituted cycloalkyl; C2 to C12 alkenyl; C3 to C12 cycloalkenyl; C3 to C12 substituted cycloalkenyl; C2 to C12 alkynyl; C6 to C12 aryl; C5 to C12 substituted aryl; polycyclic aromatics, substituted polycyclic aromatics; C6 to C12 arylalkyl; C6 to C12 alkylaryl; C3 to C12 heterocyclic; C3 to C12 substituted heterocyclic; C1 to C12 alkoxy; C1 to C12 alcohols; C1 to C12 carboxy; biphenyl; C1 to C6 alkyl biphenyl; C2 to C6 alkenyl biphenyl; or C2 to C6 alkynyl biphenyl; hydroxyl; carbonyl; amino; acetyl; acetoxy; oxo; nitro; cyano; isocyano; cyanato; isocyanato; chemotherapy compounds or derivatives thereof; tumor suppressor compounds or derivatives thereof.

In various embodiments, $R^7$ are selected from C1 to C20 alkyl; C1 to C20 substituted alkyl; C1 to C20 alkyl; C2 to C12 alkenyl; C3 to C12 cycloalkenyl; C3 to C12 substituted cycloalkenyl; C2 to C12 alkynyl; C6 to C12 aryl; C5 to C12 substituted aryl; polycyclic aromatics, substituted polycyclic aromatics; C6 to C12 arylalkyl; C6 to C12 alkylaryl; C3 to C12 heterocyclic; C3 to C12 substituted heterocyclic; C1 to C12 alkoxy; C1 to C12 alcohols; C1 to C12 carboxy; biphenyl; C1 to C6 alkyl biphenyl; C2 to C6 alkenyl biphenyl; or C2 to C6 alkynyl biphenyl; hydroxyl; carbonyl; amino; acetyl; acetoxy; oxo; nitro; cyano; isocyano; cyanato; isocyanato; chemotherapy compounds or derivatives thereof; tumor suppressor compounds or derivatives thereof.

In various embodiments, one or more of the ring carbon atoms to which $R^3$, $R^4$, $R^5$, and $R^6$ are attached can be replaced by a nitrogen, oxygen or sulfur atom.

In various embodiments, A– is defined as an anion independently selected as a halide, hydroxide, alkoxide, aryloxide, carboxylate, sulfate, phosphate, triflate, tosylate, nitrite, or borate.

In a sixth aspect, the present invention is directed to novel triphenylphosphonium substituted imidazolium salts according to the formulas:

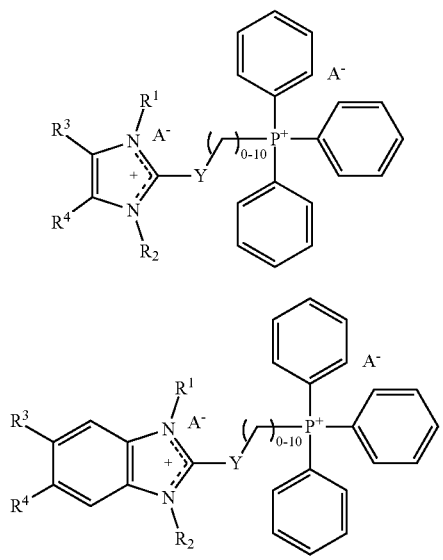

In various embodiments, $R^1$ and $R^2$ are each naphthalen-2-ylmethyl In various embodiments, $R^3$ and $R^4$, if present, are each independently selected from hydrogen; C1 to C10 alkyl; C1 to C10 substituted alkyl; C1 to C10 alkyl heteroatom groups where the heteroatom is selected from S, O, or N. C3 to C12 cycloalkyl; C3 to C12 substituted cycloalkyl; C2 to C12 alkenyl; C3 to C12 cycloalkenyl; C3 to C12 substituted cycloalkenyl; C2 to C12 alkynyl; C6 to C12 aryl; C5 to C12 substituted aryl; polycyclic aromatics, substituted polycyclic aromatics; C6 to C12 arylalkyl; C6 to C12 alkylaryl; C3 to C12 heterocyclic; C3 to C12 substituted heterocyclic; C1 to C12 alkoxy; C1 to C12 alcohols; C1 to C12 carboxy; biphenyl; C1 to C6 alkyl biphenyl; C2 to C6 alkenyl biphenyl; or C2 to C6 alkynyl biphenyl; hydroxyl; carbonyl; amino; acetyl; acetoxy; oxo; nitro; cyano; isocyano; cyanato; isocyanato.

In various embodiments A– is defined as an anion independently selected as a halide, hydroxide, alkoxide, aryloxide, carboxylate, sulfate, phosphate, triflate, tosylate, nitrite, or borate.

In various embodiments Y is defined as a carbon or sulfur atom.

In a seventh aspect, present invention is directed to a novel methine cyanine dye imidazolium salt for the effective treatment and imaging of human bladder cancer according to the structure:

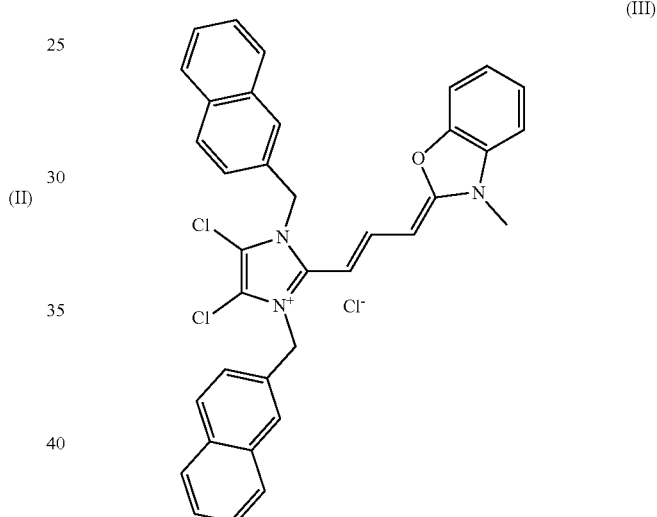

EXAMPLES

Example 1

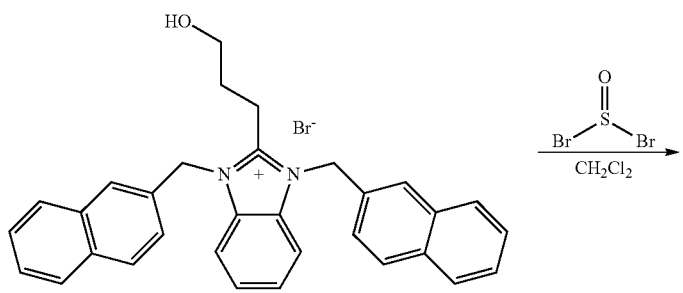

-continued

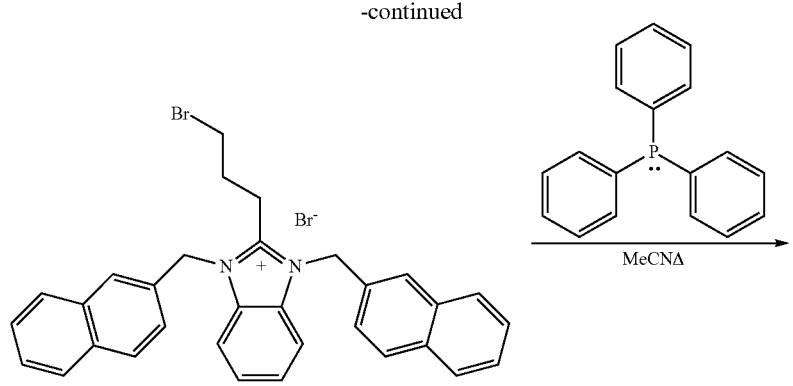

Synthesis of 1,3-bis(naphthalen-2-ylmethyl)-2-(3-(triphenylphosphonio)propyl)-1H-benzimidazolium bromide 1,3-bis(naphthalen-2-ylmethyl)-2-(3-hydroxypropyl)-1H-benzimidazol-3-ium bromide (1.01 g, 1.88 mmol) was suspended in dry dichloromethane (24 mL) and dry DMF (0.5 mL). The suspension was stirred in an icebath and thionyl bromide (1.50mL. 19.41 mmol) was added resulting in the suspension dissolving. This solution was allowed to warm to room temperature and react for 7 h. Diethyl ether was added (50 mL) producing a thick orange oil. The oil was allowed to settle and the solvent was decanted away. Additional portions (3×20 mL) of diethyl ether were added to remove any remaining thionyl bromide. The remaining oil was suspended in dry acetonitrile (50 mL) and triphenylphosphine (4.00 g, 15.27 mmol) was added changing the reaction color from orange to yellow-brown. The reaction was refluxed for 72 h after which the mixture was cooled in an ice bath. The reaction mixture was filtered and the filtrate was collected. Upon removal of solvent under reduced pressure, the product was taken up in dichloromethane and filtered to remove impurities. The product was precipitated from the filtrate with diethyl ether and collected by vacuum filtration. The solid was then washed with water (~15 mL) and recovered by vacuum filtration. The tan solid was stirred in diethyl ether for 24 h, collected by vacuum filtration, and dried under reduced pressure. (0.9896 g, 61.05%) 1H NMR (400 MHz DMSO-d6): δ 7.94-7.92 (m, 2H, Ar), 7.90-7.86 (m, 6H, Ar), 7.82-7.80 (m, 2H, Ar), 7.75-7.72 (m, 4H, Ar), 7.59-7.54 (m, 17H, Ar), 7.47 (d, 2H, Ar), 6.15 (s, 4H, CH2), 4.00 (m, 4H¬, 2-CH2), 1.88 (m, 2H, CH2). 13C NMR (125 MHz DMSO-d6): δ 153.47, 134.8 (d, J=2.8 Hz), 133.2 (d, J=10.4 Hz), 132.6, 132.4, 131.8, 131.4, 130.0 (d, J=12.5 Hz), 128.5, 127.6, 126.53, 126.50, 126.4, 125.3, 124.6, 117.6 (d, J=86.2 Hz), 113.7, 48.8, 24.2 (d, J=22.3 Hz), 20.5, 20.1 (d, J=51.2 Hz). 31P NMR (121 MHz DMSO-d6) δ 23.3. ATR-IR: 3054w, 2910w, 2862w, 1480m, 1437s, 1111m, 733w cm-1. MP=190° C.

Crystal data for C52H51Br2N2O2P: M=926.74, monoclinic, a=10.8583(2) A, b=34.0758(6) A, c=12.9337(13) A, α=90°, β=112.0353(10)°, γ=90°, V=4435.97(13) A3, T=100 (2) K, space group P2(1)/n, Z=4, 50384 reflections measured, 9015 independent reflections (Rint=0.1152). The final R1 values were 0.0502 (1>2σ(I)). The final wR(F2) values were 0.0869 (1>2σ(I)). The final R1 values were 0.1017 (all data). The final wR(F2) values were 0.1055 (all data).

Example 2

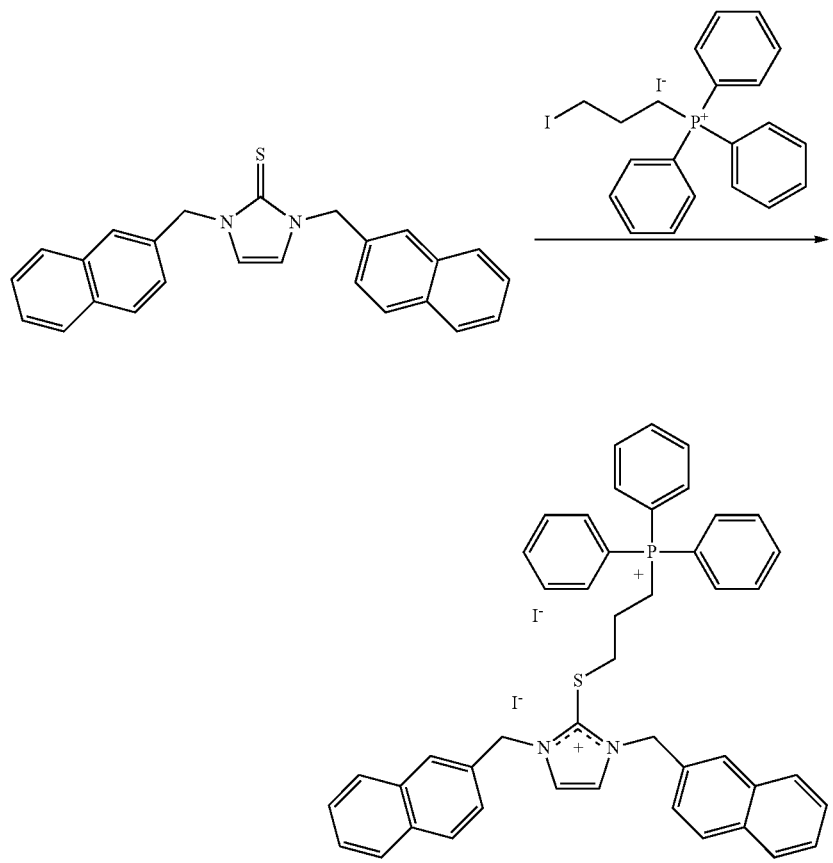

Synthesis of 1,3-bis(naphthalen-2-ylmethyl)-2-((3-(triphenylphosphonio)propyl)thio)imidazolium iodide 1,3-bis(naphthalen-2-ylmethyl)-1,3-dihydro-2H-imidazole-2-thione (0.534 g, 1.40 mmol) and (3-iodopropyl)triphenylphosphonium iodide (0.503 g, 0.901 mmol) were combined in a round bottom flask with acetonitrile (12 mL). The reaction mixture was refluxed for 120 h. Upon completion, the reaction was cooled and volatiles were removed under reduced pressure. The resulting solid was triturated in THF and collected by vacuum filtration. The crude product was recrystallized with methanol and collected by vacuum filtration. The product was dissolved in dichloromethane and washed with sodium bisulfite to remove remaining iodine. The organic layer was separated and dried. The organic solvent was removed under reduced pressure and the resulting product was collected as an off-white solid and analyzed. 1H NMR (300 MHz; DMSO-d6): δ 8.09 (s, 2H), 7.94-7.87 (m, 11H), 7.78-7.65 (m, 12H), 7.58-7.55 (m, 4H), 7.45 (dd, J=8.4, 1.2 Hz, 2H), 5.69 (s, 4H), 3.55-3.45 (m, 2H), 3.13 (t, J=7.1 Hz, 2H), 1.74-1.67 (m, 2H).

Example 3

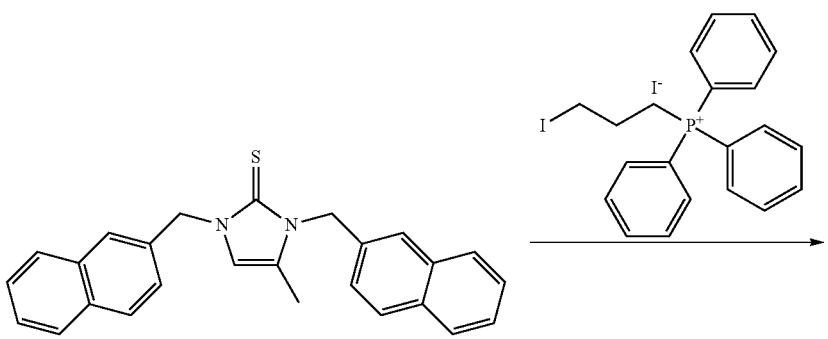

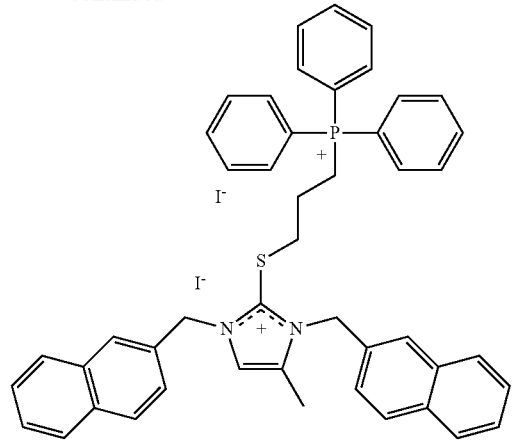

4-methyl-1,3-bis(naphthalen-2-ylmethyl)-2-((3-(triphenylphosphonio)propyl)thio)imidazol-3-ium iodide 4-methyl-1,3-bis(naphthalen-2-ylmethyl)-1,3-dihydroimidazole-2-thione (1.495 g, 3.790 mmol) and (3-iodopropyl)triphenylphosphonium iodide (1.407 g, 2.521 mmol) were combined in a round bottom flask with acetonitrile (25 mL). The reaction mixture was refluxed for 120 h. Upon completion, the reaction was cooled and diethyl ether was added to precipitate the product. The diethyl ether was decanted and the solid was triturated in THF three times. The crude product was dissolved in dichloromethane and precipitated with diethyl ether twice. The off-white solid was recovered by vacuum filtration and analyzed. 1H NMR (300 MHz; DMSO-d6): δ 7.97-7.88 (m, 11H), 7.74-7.65 (m, 13H), 7.59-7.54 (m, 4H), 7.48 (d, J=8.5 Hz, 1H), 7.34 (d, J=8.2 Hz, 1H), 5.74 (s, 2H), 5.71 (s, 2H), 3.53-3.46 (m, 2H), 3.14 (t, J=6.7 Hz, 2H), 2.21 (s, 3H), 1.74-1.68 (m, 2H).

Example 4

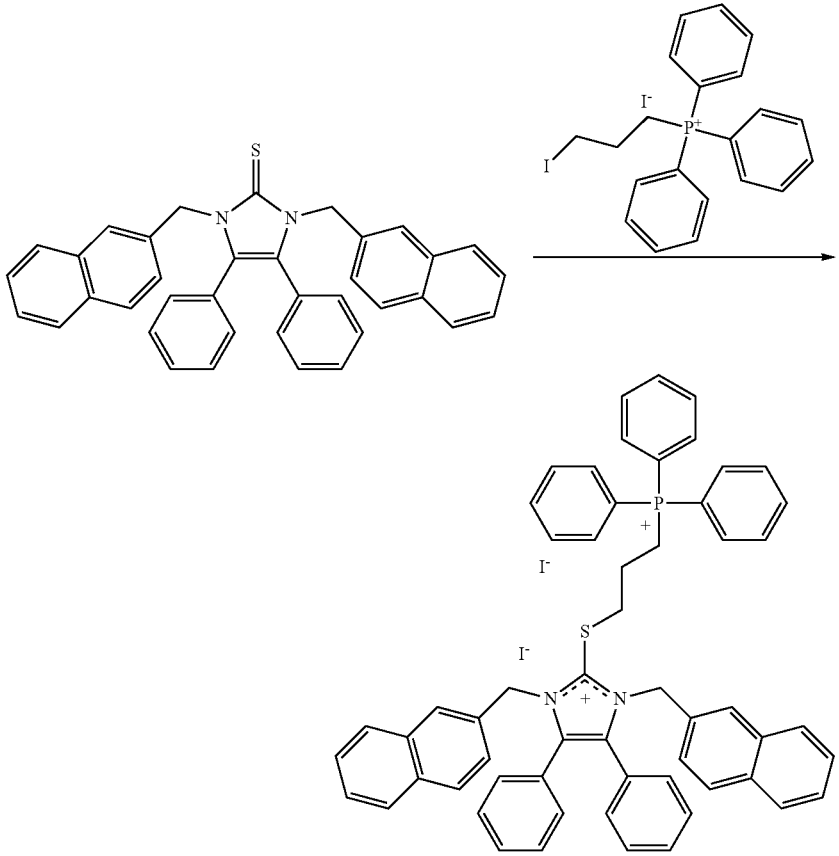

Synthesis of 1,3-bis(naphthalen-2-ylmethyl)-4,5-diphenyl-2-((3-(triphenylphosphonio)propyl)thio)imidazolium iodide.

1,3-bis(naphthalen-2-ylmethyl)-4,5-diphenyl-1,3-dihydro-2H-imidazole-2-thione (0.755 g, 1.42 mmol) and (3-iodopropyl)triphenylphosphonium iodide (1.471g, 2.635 mmol) were combined in a round bottom flask with acetonitrile (8 mL). The reaction mixture was refluxed for 72 h. Upon completion, the reaction was cooled and volatiles were removed under reduced pressure. The resulting solid recrystallized with methanol and collected by vacuum filtration. The product was dissolved in dichloromethane and washed with sodium bisulfite to remove remaining iodine. The organic layer was separated and dried. The solvent was removed under reduced pressure and the resulting product was collected as an off-white solid and analyzed. 1H NMR (300 MHz; DMSO-d6): δ 7.92-7.80 (m, 9H), 7.75-7.61 (m, 12H), 7.55-7.51 (m, 6H), 7.37-7.28 (m, 10H), 7.24 (dd, J=8.5, 1.2 Hz, 2H), 5.72 (s, 4H), 3.50-3.41 (m, 2H), 3.29 (t, 2H), 1.74-1.67 (m, 2H).

Example 5

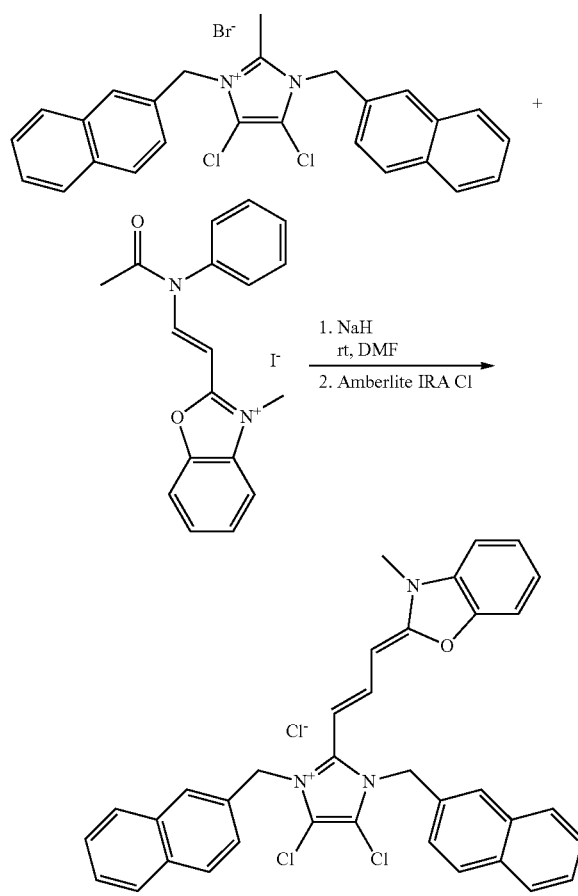

Synthesis of 4,5-dichloro-2-((1E,3Z)-3-(3-methylbenzoxazol-2(3H)-ylidene)prop-1-en-1-yl)-1,3-bis(naphthalen-2-ylmethyl)-1H-imidazolium chloride (III)

4,5-dichloro-2-methyl-1,3-bis(naphthalen-2-ylmethyl)-1H-imidazolium bromide (0.500 g, 0.976 mmol) was stirred at room temperature in dry DMF (20 mL) with sodium hydride (0.0509 g, 2.12 mmol). After 30 minutes (E)-3-methyl-2-(2-(N-phenylacetamido)vinyl)benzoxazol-3-ium iodide (0.413 g, 0.983 mmol) was added and the reaction mixture was allowed to stir for 24 h. Crude product was precipitated with excess diethyl ether and collected via vacuum filtration. The resulting product was washed with 30 mL of water to remove any sodium salts. The crude product was chromatographed on silica gel (70:30 CHCl3/EtOH). The product was stirred in THF to remove any residual impurities and the solide was obtained by vacuum filtration. The bright yellow solid was then dissolved in methanol and passed through an Amberlite IRA-400 Cl anion exchange column. The volatiles were removed and the product was washed with THF, producing the final product. (0.299 g, 30.6%) 1H NMR (400 MHz DMSO-d6): δ 8.09 (2H, d, Ar) 7.99 (4H, m, Ar) 7.87 (2H, s, Ar) 7.58 (6H, m, Ar) 7.32 (1H, dd, alkene, j=12.3 Hz) 7.21 (2H, m, Ar, j=7.2 Hz) 7.03 (1H, dd, Ar, j=7.8 Hz) 6.63 (1H, d, Ar, J=8.2Hz) 6.02 (1H, d, alkene, J=15.2 Hz) 5.68 (4H, s, CH2) 5.16 (1H, d, alkene, J=11.7 Hz) 3.28 (3H, s, CH3). 13C NMR (100 MHz DMSO-d6): δ 159.9, 146.8, 145.5, 141.6, 132.9, 132.5, 132.4, 131.7, 128.9, 127.8, 127.6, 126.6, 126.4, 124.6, 124.5, 124.0, 122.4, 117.4, 109.0, 108.6, 90.9, 77.3, 50.2, 29.1. TOF MS ESI m/z: 587.8887, calc. exact mass for C50H36AgCl4N4+=588.1604. ATR-IR: 3019w, 2937w, 1640w, 1620w, 1599w, 1560m 1196m cm−1.

Crystal Data for C36H30Cl3N3O2: M=642.98, triclinic, a=10.1036(3) AÅ, b=10.2309(3) Å, c=16.2459(4) Å, α=99.954(2)°, β=98.123(2)°, γ=107.477(2)°, V=1543.96(7) Å3, T=100(2) K, space group P-1, Z=2, 16037 reflections measured, 4782 independent reflections (Rint=0.0399). The final R1 values were 0.0372 (I>2σ(I)). The final wR(F2) values were 0.0849 (I>2σ(I)). The final R1 values were 0.0527 (all data). The final wR(F2) values were 0.0920 (all data).

Example 6

Methodology of the Evaluation of In Vitro Anti-Cancer Activity

MTS Assay:

Select bladder cancer cell lines (RT112, UMUC3, and J82) were seeded at 5000 cells/well in 96 well plates and incubated for 24 h. Cells were treated with compound in media at a concentration of 15.625 µM to 1000 µM dissolved in two-fold increments or no drug for either 30 min or 1 h and the media was replaced with 100 µL normal growth media. After 24 h, 20 µL of MTS (2 mg/mL) and PMS (0.05 mg/mL) was added to each well, incubated for 1 h, and the absorbance was measured at 490 nm. Average absorbance (i.e. cell viability) was then plotted as a percentage of average control well absorbance. All treatments were performed in quadruple.

All subsequent treatments of RT112, UMUC3, and J82 cells or normal human urothelial cell (NHUC; generous gift from Maggie Knowles, PhD; University of Leeds) were performed 1 day after seeding and for 1 h using select compounds. Cells and cell fragments were collected 24 h later.

CellTiter -Glo® Assay:

Select bladder cancer cell lines were seeded at 10,000 cells/well in black-walled 96 well plates and incubated for 24 h. Cells were treated with compound in their respective media (as recommended by ATCC) at concentrations of 500 to 7.8 µM dissolved in two-fold dilution increments or vehicle for 1 h, followed by replacement of treatment media with normal growth media. After 24 h, plates with cells were incubated at room temperature for 30 min, followed by the addition of 20 μL of CellTiter-Glo® luminescent cell viability assay reagent (Promega) and mixing. After 2 min of incubation at room temperature, luminescence for each plate was measured using IVIS. Relative survival for each treatment group was calculated using vehicle control. All treatments were performed in quadruplicate.

Colony Forming Assay:

Cells were seeded at 500 cells/well in 6-well plates in triplicate for each treatment. Cells were allowed to grow in normal media for 10 days. Cells were stained with crystal violet (0.5% crystal violet in 20% MeOH/water), incubated at 4° C. for 5 min, washed several times with DI water, and dried prior to imaging.

Sub-G1 Analysis:

Cells were seeded in 6-well plates at 300,000 cells/well, in triplicate for each treatment. Media and cells were collected and washed with 1% FBS in PBS. Washed cells were suspended in 0.5 mL PBS and fixed with 5 mL cold 70% ethanol, followed by incubation at 4° C. for 30 min protected from light. Cells were pelleted, washed, incubated at room temperature in phosphate citric acid buffer, re-pelleted, and resuspended in propidium iodide (PI)/RNase solution and analyzed. The stained cells were analyzed using a BD FACScan™ flow cytometer for sub-G1 populations using the appropriate gating parameters.

Western Blot Analysis:

Cells were seeded at 300,000 cells/well in a six well plate. Cells and floating debris were pelleted, washed with PBS, and lysed in RIPA buffer with protease inhibitors. Cell lysate (30 μg protein) was mixed in sample buffer containing 50 mM DTT and incubated at 95° C. for 10 min. Proteins were separated using SDS-PAGE and transferred to a nitrocellulose membrane. The membrane was blocked with milk, stained with PARP (Cell Signaling Technology, #9542), caspase 9 (Cell Signaling Technology, #9502) and Ran (BD Biosciences, #610340) primary antibodies for 1 h, and washed. HRP-conjugated secondary antibodies (Invitrogen, #31430 and #31460) were added and incubated for 1 h. The bands were detected using an Amersham™ ECL kit (GE Life Sciences) and imaged on FluorChem E Digital Darkroom.

Preliminary Results:
Compound Tested

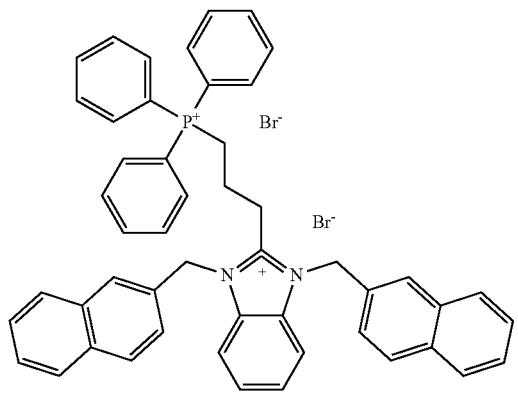

The compound was evaluated in the National Cancer Institute's (NCI) Developmental Therapeutics Program (DTP) 60 human tumor cell line one-dose assay. Cells in the assay are exposed to the tested compound at a single dose of 10 μM and results are presented as a growth percentage relative to the initial number of cells at the beginning of the study and to the non-treated control cells. Values for growth percent range from −100 (complete cell death) to 100 (no growth inhibition) with a value of zero meaning that there is no overall growth of the cells. Full experimental details can be found on the NCI's DTP webpage (https://dtp.cancer.gov/discovery_development/nci-60/methodology.htm).

Results of the assay show that not only are the growth percent values highly varied between different groups of cell lines, but are highly varied between different cell lines of the same type of cancer. For example, growth percent values on the melanoma cell lines ranged from 13.81 for LOX IMVI, to 37.11 for SK-MEL-28, and 100.09 for SK-MEL-2. The variability between cell lines of the same type of cancer could prove to be very important for future studies that are aimed at identifying the exact mechanism of action of the compound or those that are similar.

For imidazolium compounds to be practical and effective intravesical therapies for bladder cancer, they must elicit a cell-killing effect after exposure for 1 hour or less. Patients cannot retain a drug for long periods, and this likely contributes to the ineffectiveness of intravesical chemotherapy. Therefore the growth inhibition of the compound was assessed at various concentrations against different bladder cancer cell lines at 30 min and 1 h. As expected, the GI50 concentration was higher than previously calculated after continuous 48 h exposure from the NCI-60 cell line screening. Increase in exposure time from 30 to 60 min decreased the cell viability slightly in all three cell lines (see FIG. 1 parts A through D). J82 cells seemed slightly more sensitive to the compound than RT112 or UMUC3 cells.

FIG. 1 shows growth inhibition to RT112 (A), UMUC3 (B) and J82 (C) bladder cancer cell lines at 30 min and 1 h exposure times. The estimated GI50 values for each cell line showed exposure-time dependent cytotoxicity (D).

The long-term cytotoxicity of the compound on bladder cancer cell lines was assessed using a colony-forming assay. No colonies formed after treatment with the compound for 1 h at the GI50 (500 μM) for all cell lines or after 250 μM treatment for RT112 and UMUC3 cell lines, while J82 cell line had few colonies.

To determine if the compound caused growth inhibition or cell death, propidium iodide staining was performed followed by flow cytometry to measure the amount of late phase apoptotic cells (sub-G1 fraction). All three cell lines had significant amounts of apoptotic events compared to vehicle-treated cells. RT112 and NHUC cell lines had a lower percentage of apoptotic cells after a 500 μM treatment than when treated with 250 μM. This may be due to the extreme and rapid toxicity of the higher dose (see below).

To confirm the mechanism of toxicity was apoptosis, RT112 cells and cell debris were collected immediately after or 24 h after the end of treatment and cleaved PARP (c-PARP) and cleaved caspase-9 (c-Casp9), both markers of apoptosis, were measured using immunoblot. The amount of c-PARP after the treatment was higher immediately after treatment than at 24 h, while the amount of Ran was greatly depleted immediately after treatment and further decreased with increasing doses after 24 h. In addition, c-Casp9 was detected after treatment with a 250 μM dose immediately after treatment, but was absent immediately after treatment with a 500 μM dose or 24 h after either dose. Caspase-9 is cleaved during mitochondrion-triggered apoptosis to initiate the cell death cascade. This suggests that RT112 cells undergo apoptosis with such briskness that the detectable signal is disintegrated after 24 h due to cell fragmentation.

Compound Tested

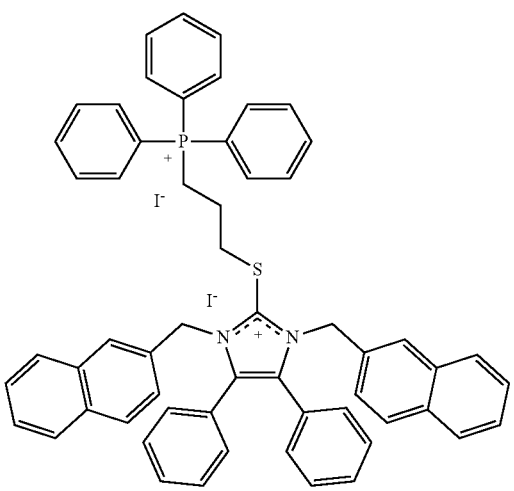

Another triphenylphosphonium substituted salt with a sulfur included in the C2 alkyl chain was evaluated for growth inhibition against select bladder cancer cell lines. The results of this study indicate a much more cytotoxic imidazolium salt with roughly 3 fold more activity against J82 cell line than the previously discussed triphenylphosphonium imidazolium salt. Overall this compound averaged significantly more cytotoxicity.

Figure 2:
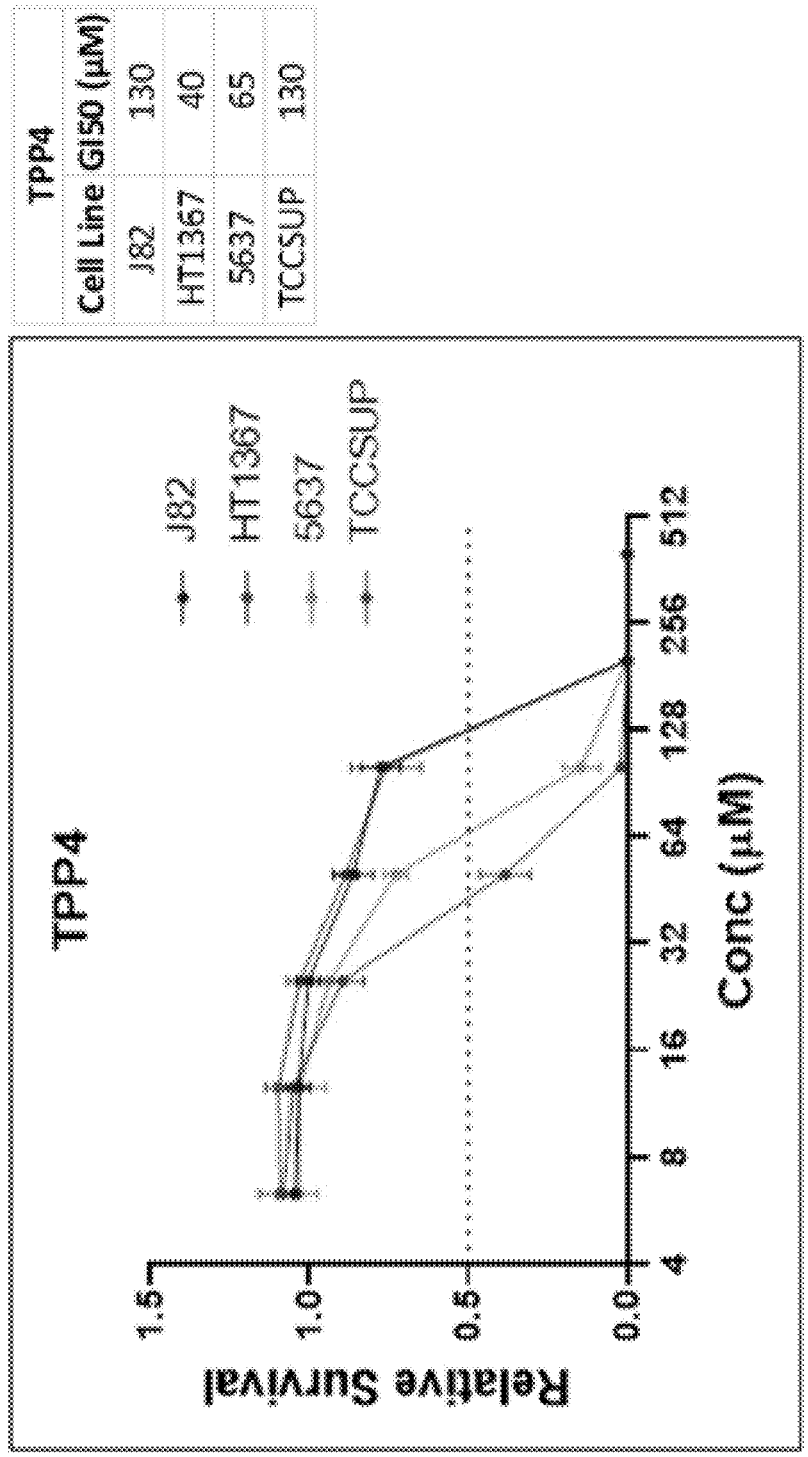
FIG. 2 provides growth inhibition of an imidazolium compound of this invention as assessed at various concentrations against different bladder cancer cell lines at 1 h exposure times and the estimated GI50 values for each cell line.

FIG. 2 shows growth inhibition to J82, HT1367, 5637, and TCCSUP bladder cancer cell lines at 1 h exposure times. The estimated GI50 values for each cell line are shown. In order to determine if this more cytotoxic compound may be an effective treatment, the long term cytotoxicity was evaluated by colony forming assays. The 5637 and HT1367 cell lines were extremely susceptible to the compound as a 1 h treatment with 40 µM resulted in no cancer growth after 10 days incubation. Furthermore in J82 cancer cell lines, treatment of the cells with 160 µM dose resulted in inhibition of cell growth after 10 days.

Compound Tested:

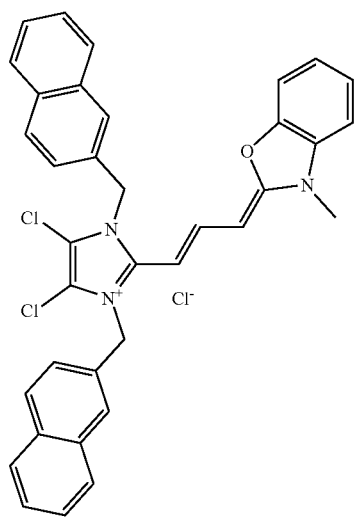

(III)

Figure 3:
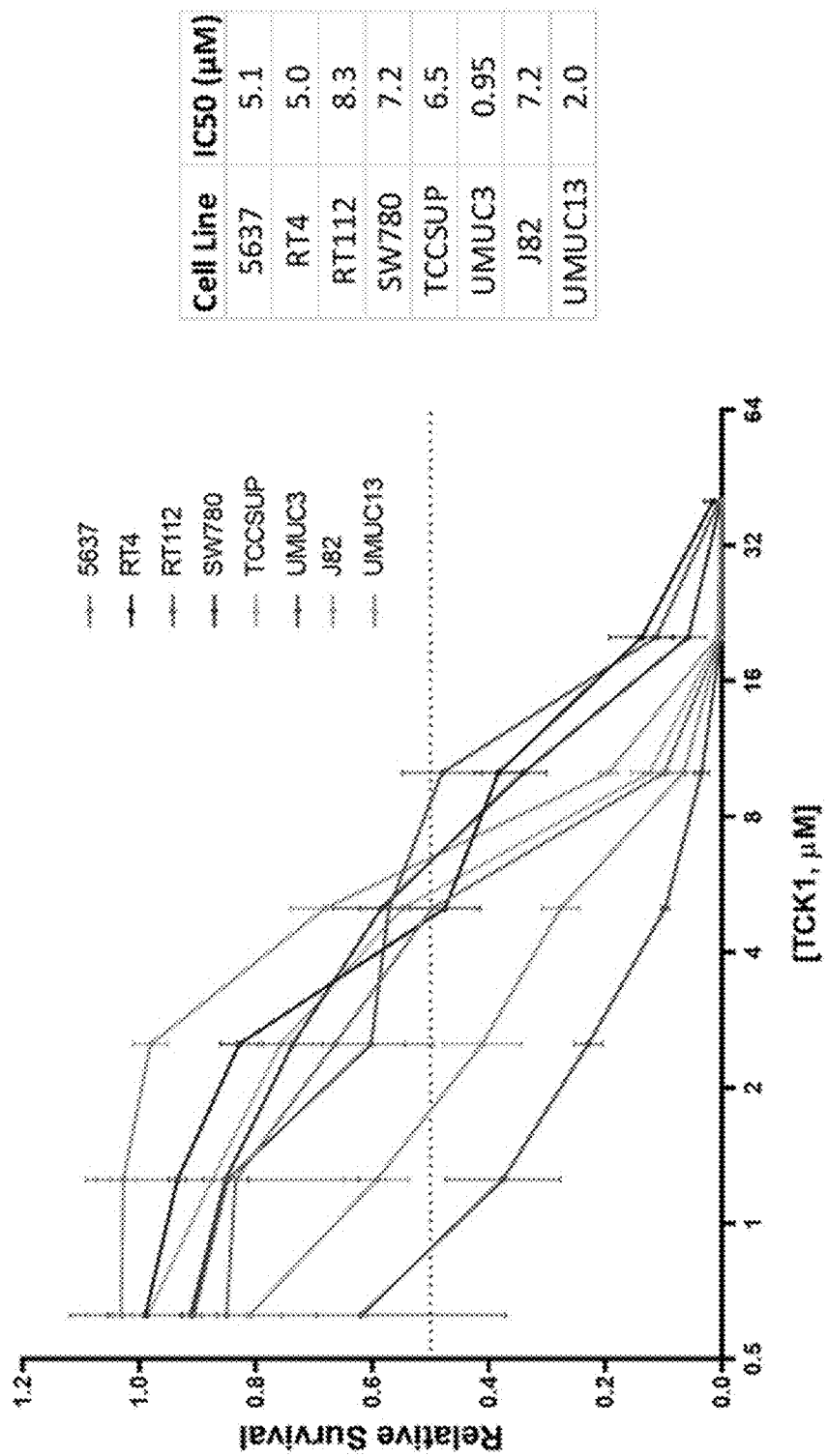
FIG. 3 provides growth inhibition of an imidiazolium compound of this invention as assessed at various concentrations against different bladder cancer cell lines at 1 h exposure times and the estimated GI50 values for each cell line.

Similar to the previous studies, the growth inhibition the theronaustic cell killer (TCK) was evaluated over a time period of 1 h (see FIG. 3). The compound exhibited extremely lower GI50 concentrations than both of the triphenylphosphonium compound, previously discussed.

Figure 4:
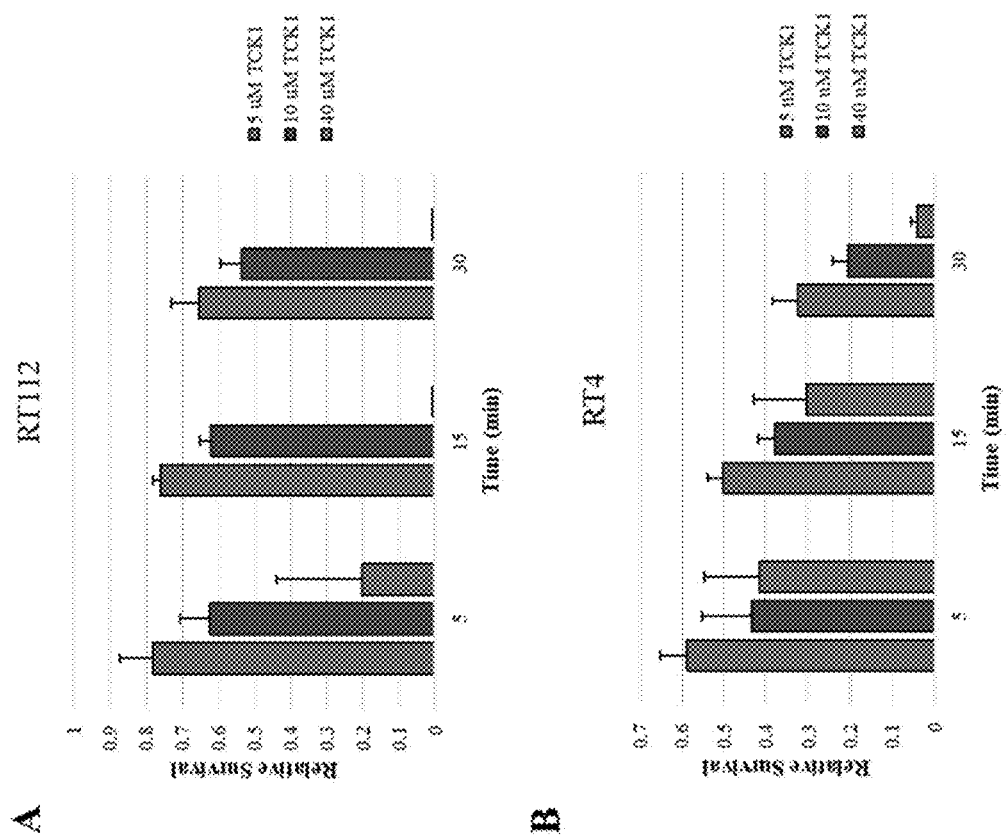
FIG. 4 provides the relative survival of RT4 cells in part A and RT112 cells in part B that were treated with varying concentrations of III for different exposure times followed by a 24 h recovery.

With the remarkable potency determined by the CellTiter-Glo® Assay, the cell lines RT4 and RT112 were evaluated for relative survival when treated with varying concentration of the compound and exposure time (See FIGS. 4 A and B). It was determined that III inhibits cell survival at a 40 µM concentration after a 5 min exposure time in the RT112 cell line and a 10 µM concentration after a 5 min exposure time in the RT4 cell line.

Due to the TCK compound having enhanced cytotoxicity as well as being a fluorescent dye, confocal microscopy images of RT112 bladder cancer cells were stained with the compound. The compound has a very broad fluorescence profile ranging from green to red, therefore it can be exploited to determine the cellular target of lipophilic imidazolium salts. RT112 cells were stained with the TCK compound and Mitoview™ green. Upon excitation with the corresponding wavelengths for each dye, it was determined that the TCK compound localizes in the mitochondria.

Figure 5:
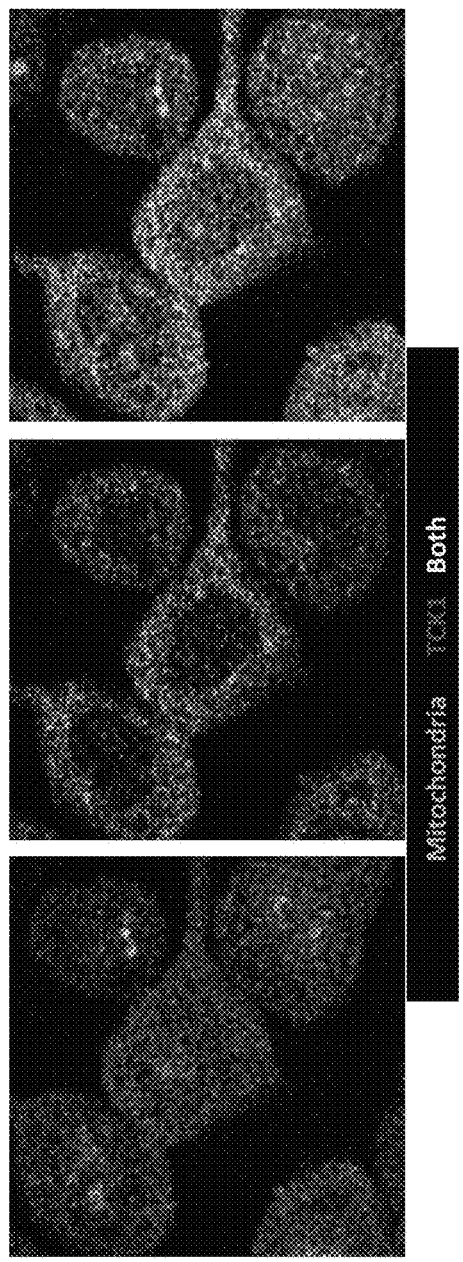
FIG. 5 provides confocal microscopy images of RT112 bladder cancer cells treated with the TCK compound and Mitoview™ green.

FIG. 5 shows confocal microscopy images of RT112 bladder cancer cells treated with the TCK compound and Mitoview™ green. The overlap of the fluorescence profile indicates the TCK compound localizes in the mitochondria.

Compound Tested:

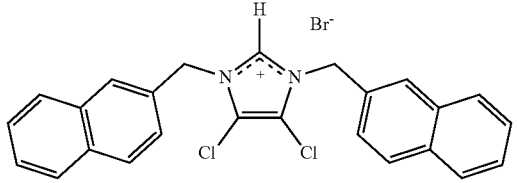

As stated previously, the cell-killing effect must occur within a short time period to be an effective bladder exfoliant and treatment for bladder cancer. As a comparison to previously tested imidazolium salts, the growth inhibition of the first imidazolium salt developed by the Youngs group was evaluated over a time period of 30 min and 1 h (see FIG. 6 parts A through D). The compound exhibited much lower GI50 concentrations than the previously discussed compounds, with the exception of the methine cyanine imidazolium salt proved to be much more cytotoxic.

Figure 6:
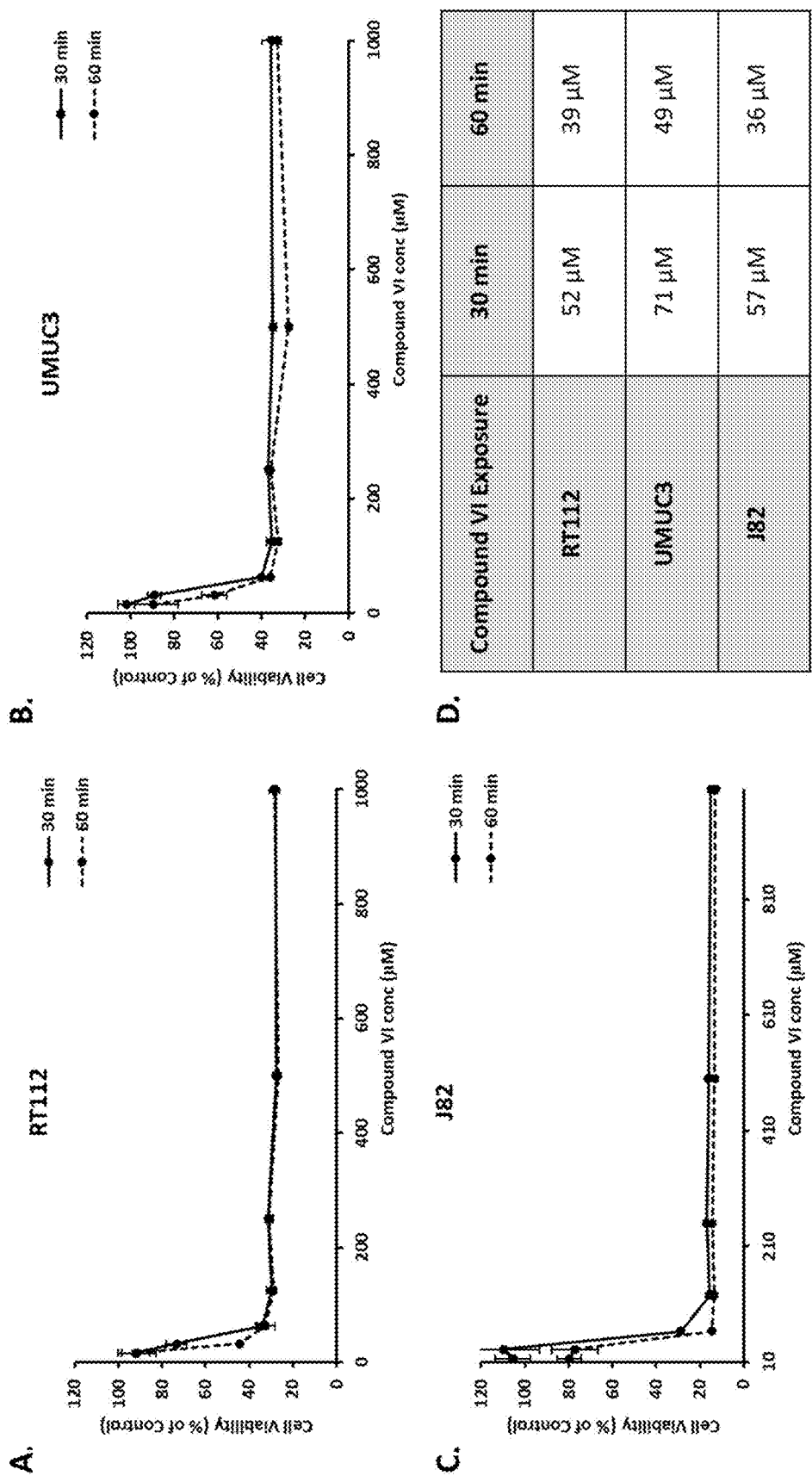
FIG. 6 provides growth inhibition of an imidiazolium compound of this invention as assessed at various concentrations against different bladder cancer cell lines at 30 min and 1 h exposure times, with growth inhibition to RT112 shown in part A., to UMUC3 shown in part B., and to J82 shown in part C. The estimated GI50 values for each cell line showed exposure-time dependent cytotoxicity in part D.

FIG. 6 shows growth inhibition to RT112 (A), UMUC3 (B) and J82 (C) bladder cancer cell lines at 30 min and 1 h exposure times. The estimated GI50 values for each cell line showed exposure-time dependent cytotoxicity (D).

Furthermore, the compound was evaluated by the colony forming assay to determine the long-term growth inhibition against select bladder cancer lines. The results of the study showed the GI50 concentration nearly eradicates all cancer after 10 days. Adversely to the previous compound the ½ GI50 concentration does not completely inhibit cell growth allowing colonies to form after 10 days. Furthermore, it was concluded that the J82 cell line was more resistant to the long-term cytotoxicity at the GI50 concentration.

As with the triphenylphosphonium compound previously discussed, the imidazolium salt listed above was evaluated for mode of cell death by sub-G1 analysis. The results of the study show that the mechanism of death is likely apoptosis given the high fraction of sub-G1 events occurring 24h after a 1-hour treatment with this compound.

Figure 7:
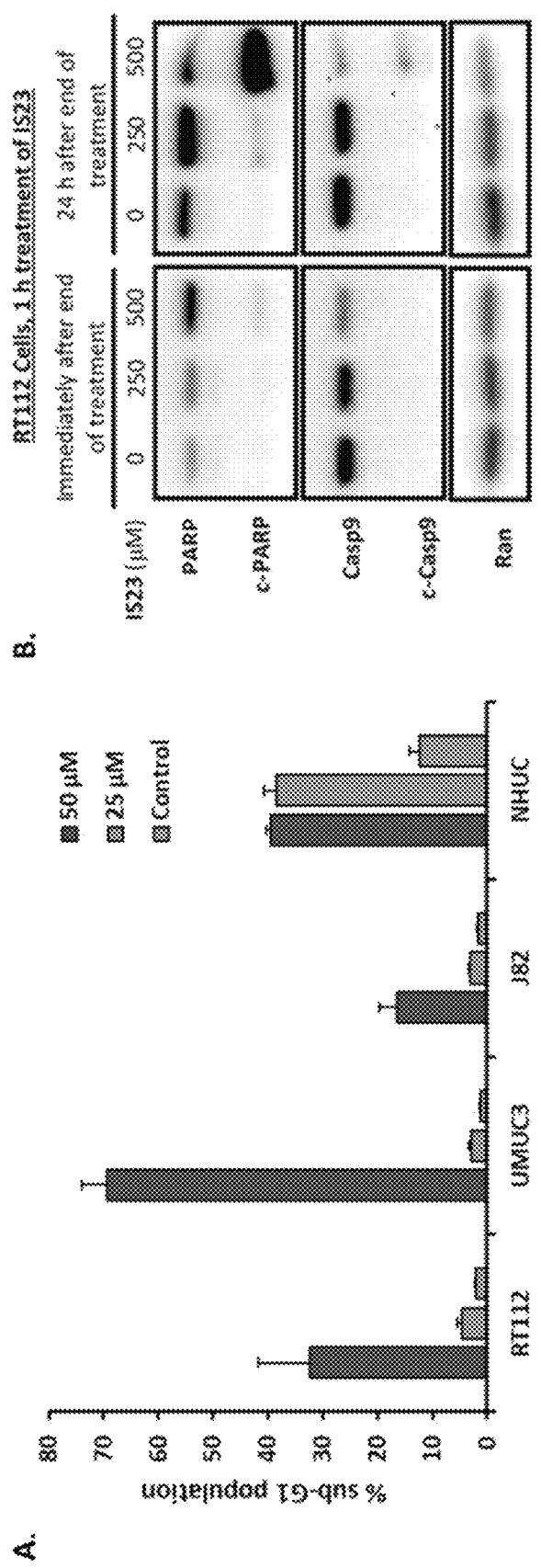
FIG. 7 provides cell cycle analysis of bladder cancer cell lines and NHUC were used to measure the sub-G1 population 24 h after 1 h exposure to various concentrations of compound in part A and western blots revealing that RT112 cells underwent PARP cleavage (c-PARP) and caspase-9 cleavage (c-Casp9) after treatment with compound in part B.

FIG. 7 shows (A) Cell cycle analysis of bladder cancer cell lines and NHUC were used to measure the sub-G1 population 24 h after 1 h exposure to various concentrations of the compound. (B) Western blots revealing that RT112 cells underwent PARP cleavage (c-PARP) and caspase-9 cleavage (c-Casp9) after treatment with compound.

The Western blot of RT112 cell lysates immediately or 24h after 1 h treatment with this compound again show significant induction of cleaved PARP1 and Caspase 9, reliable markers that the cells are undergoing apoptosis, most likely via a mitochondrion-triggered pathway.

Example 7

Methodology of the Evaluation of In Vivo Anti-Cancer Activity

Compound Tested:

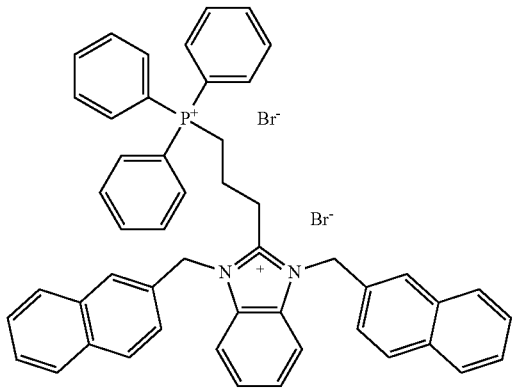

In Vivo Studies in Healthy Murine Models:

Intravesical treatment of mice was achieved by anesthetizing three test groups of mice. The mice were inoculated with two 100 μL doses at concentrations of 750 μM or 1500 μM compound in 10% DMSO, or 10% DMSO vehicle solution over a 24 h period. The treatments were retained intravesically for 1 h under anesthesia. 24 h after the last treatment, the mice were sacrificed and histology was performed on formalin-fixed bladders.

In Vivo Studies in Murine Bladder Cancer Model:

Mice were treated with 0.05% BBN in drinking water for a period of 10 weeks followed by 5 weeks of normal drinking water. Contrast-enhanced CT-urography was performed prior to the first treatment and the population was divided into three cohorts. Mice were treated intravesically with two 100 μL doses at concentrations of 750 μM, 1500 μM in 10% DMSO, or 10% DMSO vehicle solution with 24 h in between each dose. The treatments were retained intravesically for 1 h under anesthesia. Contrast-enhanced excretory CT-urography was performed every 2 weeks for 8 weeks.

Preliminary Results:

Histolopathological analysis of the bladder in the healthy mice test groups at 750 or 1500 μM revealed little cytotoxicity (dark area; towards the lumen; cells lining the white space). In comparison to the vehicle control (1.5% DMSO) there was little change in the bladder epithelium between the imidazolium salt and the negative control. There was also no apparent immune infiltration or inflammation. These results lead to the conclusion that when compound is used for intravesical therapy in normal murine models, little effect on healthy urothelium occurs.

In a second set of experiments, mice were induced to develop bladder cancer by treatment with BBN, then monitored by contrast-enhanced excretory CT urography to visualize bladder filling defects (presumptive tumors or pre-cancerous lesions). CT-urography of the DMSO control group (FIG. 8) showed filling defects beginning 0-2 weeks after the end of BBN treatment (denoted by solid white arrows). These presumptive tumors or pre-cancerous lesions were monitored over a period of 8 weeks. All vehicle-treated mice had filling defects by week 4, and the masses continued to grow in size. In comparison, excretory urography of mice treated with 750 μM compound (FIG. 9) showed no filling defect in two of four mice after 8 weeks. One mouse developed a tumor during the 8 week follow up period, and one mouse that had a detectable filling defect tumor prior to treatment with the compound maintained the tumor but it did not grow or shrink. Excretory urography of mice treated with 1500 μM intravesical compound revealed that two of four mice did not develop any new filling defects after the discontinuation of BBN (FIG. 10). One mouse developed one filling defect beginning at week 8 and one mouse had a filling defect prior to treatment with the compound which continued to grow after treatment.

Due to the brisk and effective induction of cell death in bladder cancer cell lines, with the absence of histological damage in the normal bladder of murine models after intravesical instillation, we hypothesized that the triphenylphosphonium salt would behave as a selective agent for cancerous tissue versus normal tissues in a murine bladder cancer model. To test this hypothesis, tumors were induced in murine bladders by the addition 0.05% BBN in drinking water until a bladder tumor was identified. The presence of tumors in the bladders of the mice were confirmed by excretory μCT urography. Anesthetized mice with bladder tumors were then treated for 1 h with 1500 μM of the compound, and histology and immunohistology was performed to stain the apoptotic marker, cleaved caspase-3. Mice treated with the compound showed significantly higher levels of cleaved caspase-3 in the locations that had a significant amount of hyperplasia, dysplasia and necrosis Cleaved caspsase-3 was not appreciably detected in the normal adjacent urothelium in compound-treated mice with tumors. Cleaved caspase-3 was also not appreciably detected in the tumor, or in the adjacent normal urothelium of the vehicle control group. This shows that the triphenylphosphonium compound induces apoptosis in cancer cells without harming normal cells in the bladder.

Figure 8:
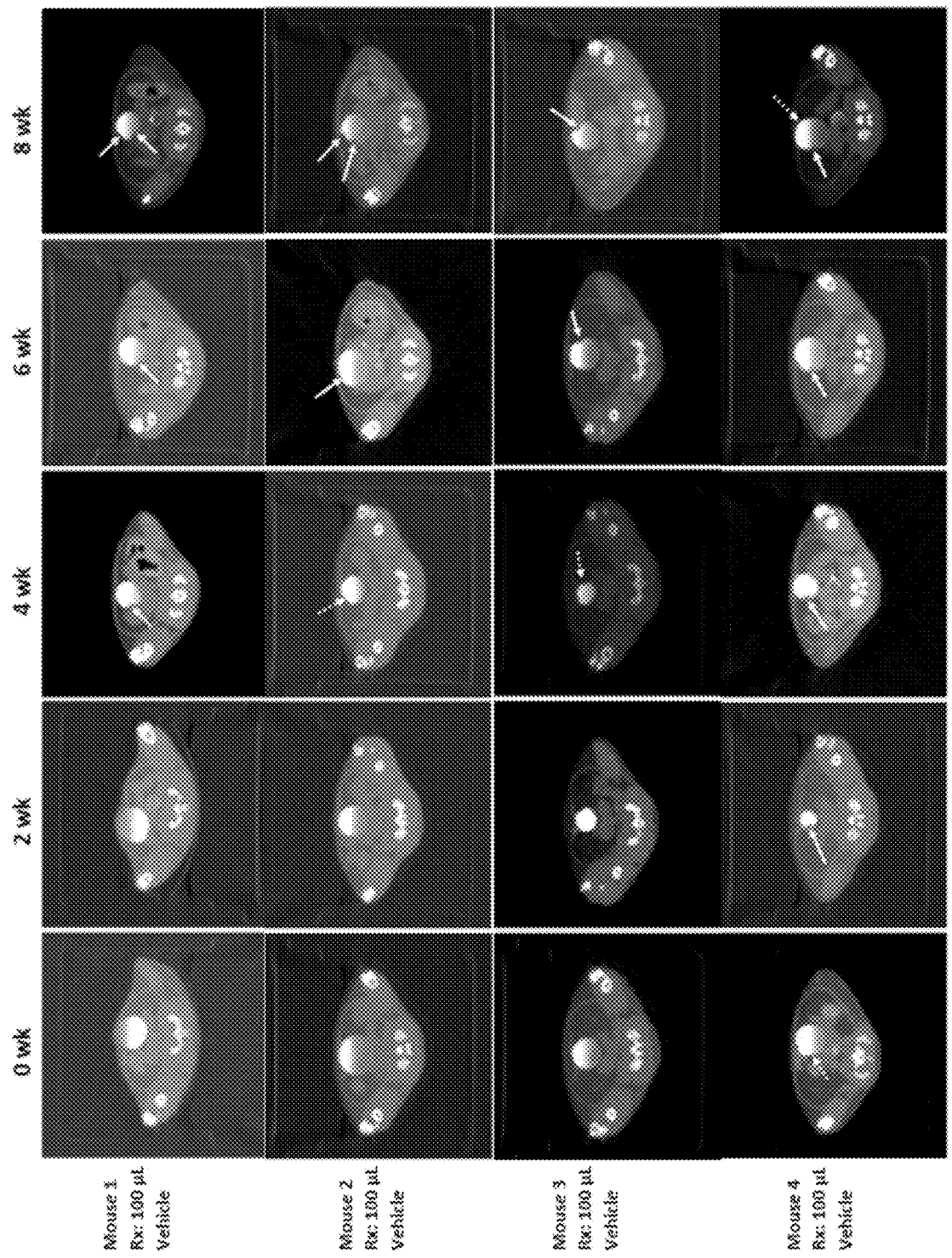
FIG. 8 provides CT-urograms of DMSO vehicle treated mice over a period of 8 weeks.

FIG. 8 shows CT-urograms of DMSO vehicle treated mice over a period of 8 weeks. Solid white arrows indicate definite filling defects, and dotted white arrows demonstrate equivocal filling defects.

Figure 9:
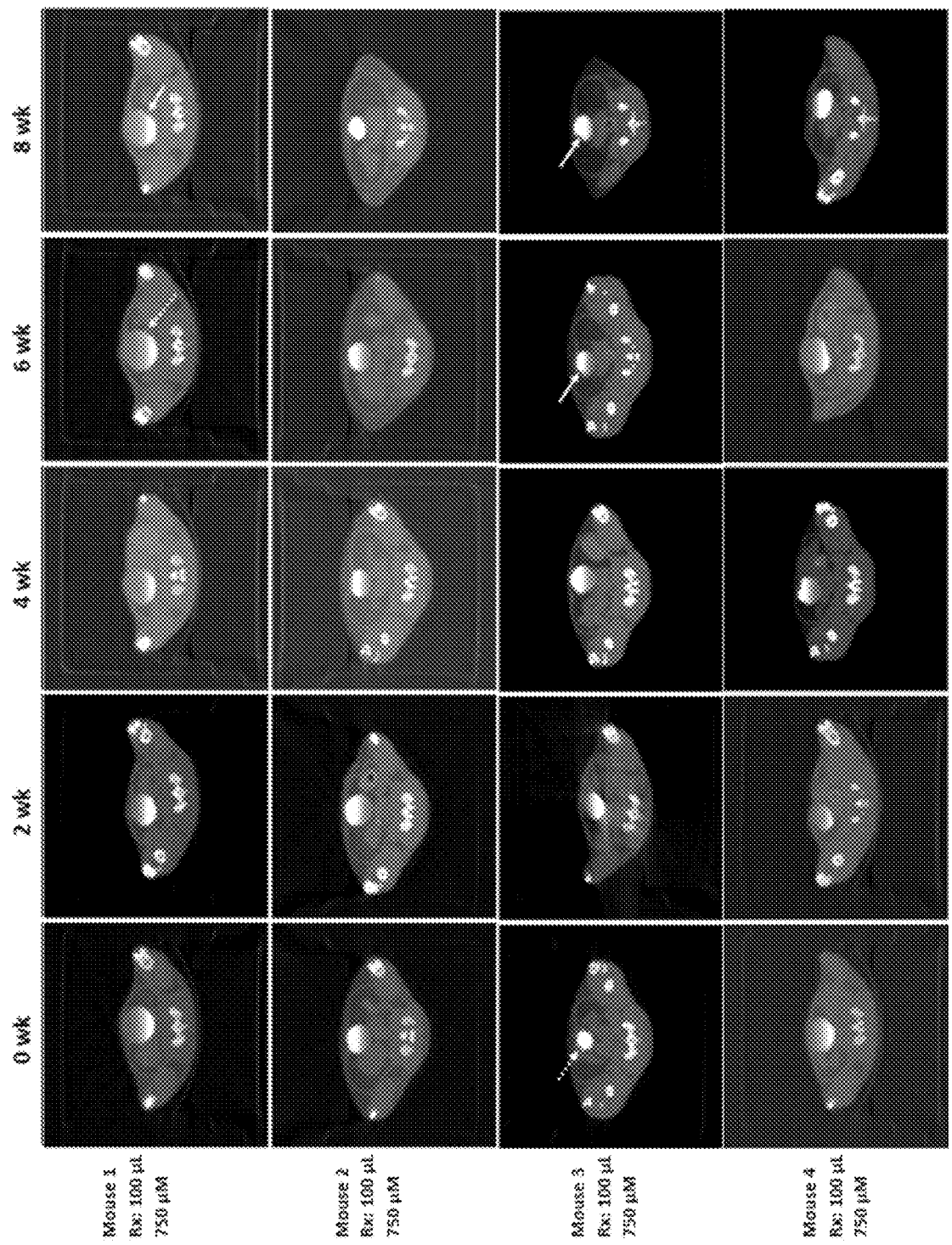
FIG. 9 provides CT-urograms of 750 μM treated mice over a period of 8 weeks.
Figure 10:
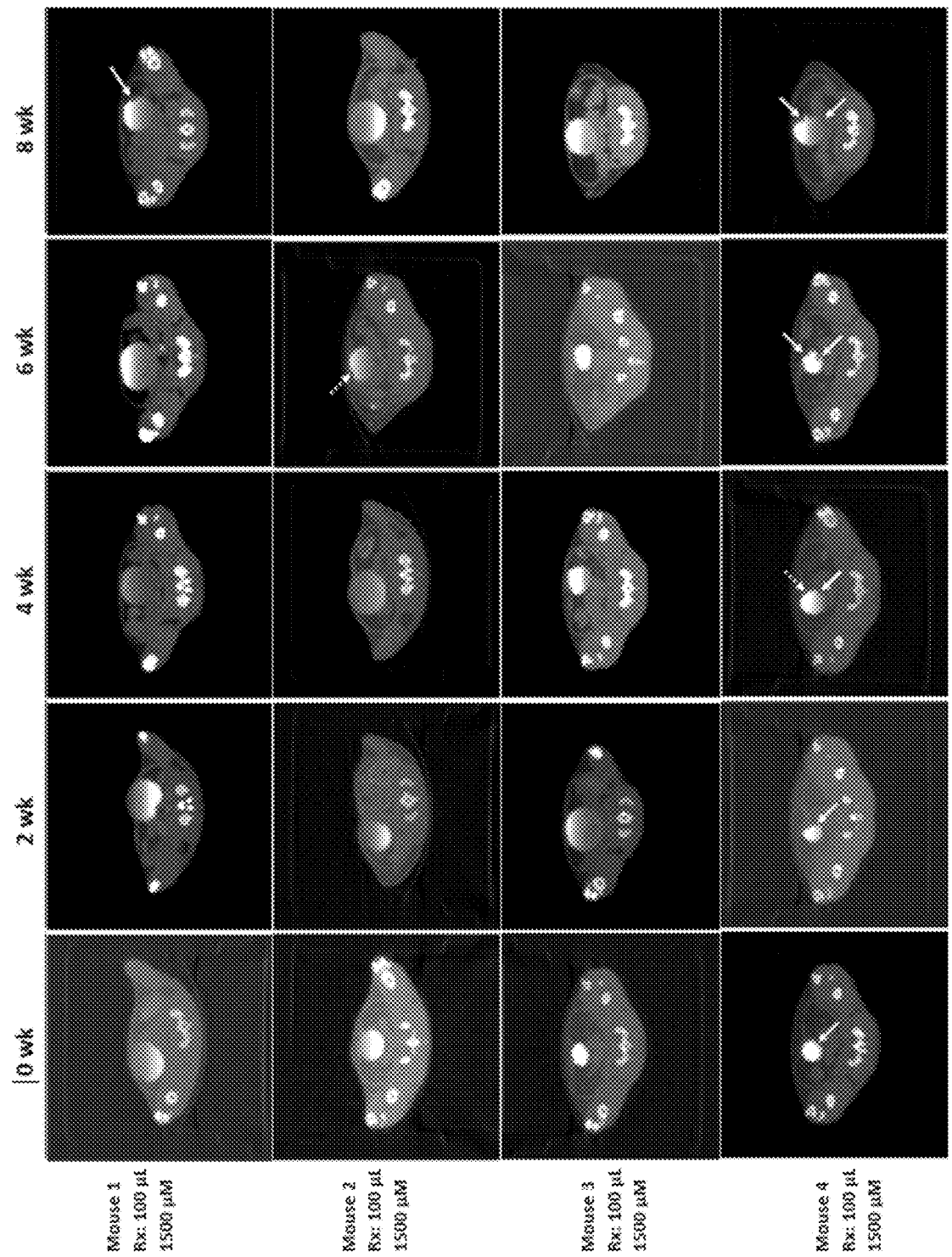
FIG. 10 provides CT-urograms of 1500 μM treated mice over a period of 8 weeks.

FIG. 9 shows CT-urograms of 750 μM treated mice over a period of 8 weeks. Solid white arrows indicate definite filling defects, and dotted white arrows demonstrate equivocal filling defects.

FIG. 10 shows CT-urograms of 1500 μM treated mice over a period of 8 weeks. Solid white arrows indicate definite filling defects, and dotted white arrows demonstrate equivocal filling defects.

Figure 11:
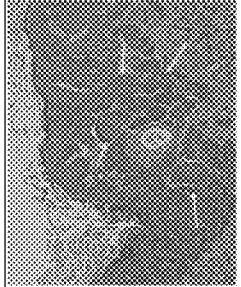
FIG. 11 provides a histology of bladders treated with Vehicle.

FIG. 11 shows a histology of bladders treated with Vehicle. Bladders were harvested after 8 weeks.

Figure 12:
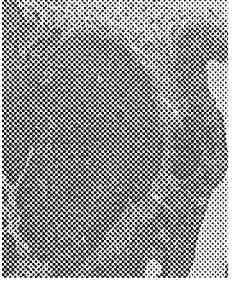
FIG. 12 provides a histology of bladders treated with 1500 μM.

FIG. 12 shows a histology of bladders treated with 1500 µM. Bladders were harvested after 8 weeks.

Example 8

Compound Tested:

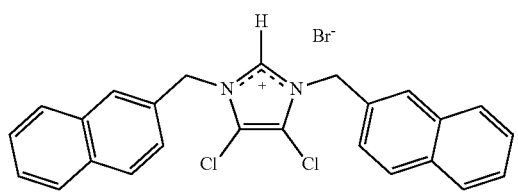

In Vivo Studies in Healthy Murine Models:

Intravesical treatment of mice was achieved by anesthetizing three test groups of mice. The mice bladders were treated intravesically with two 100 µL doses of compound at 800 µM in 25% DMSO or 25% DMSO vehicle solution over a 24 h period. The treatments were retained intravesically for 1 h under anesthesia. After 24 h the mice were sacrificed and histology was performed on the bladders.

In Vivo studies in Murine Bladder Cancer Model:

Mice were treated with 0.05% BBN in drinking water for a period of 10 weeks followed by 4 weeks of normal drinking water. Contrast-enhanced CT-urography was performed prior to the first treatment and the population was divided into three cohorts. The mice were treated intravesically with 100 µL of compound at 800 µM (for female mice) or 50 µL of compound at 1600 µM (for male mice) to account for dilution due to our inability to completely drain the male bladder. Mice were treated two times with a rest period of 24 h. Contrast-enhanced excretory CT-urography was performed every 2 weeks for 4 weeks.

Preliminary Results

Unlike the triphenylphosphonium compound previously discussed, the select compound is untargeted toward cancer and the bladder histology of healthy mice treated with 800 µM compound displayed significant urothelial thinning and exfoliation. In comparison to the vehicle control (DMSO), complete and partial exfoliation was observed after treatment with 800 µM compound.

With the exfoliative properties of the compound observed in healthy mice and an effective dose determined, murine bladder cancer models were tested. The results of the study showed that two vehicle-treated mice exhibited filling defects by excretory CT, and histology confirmed that either pre-cancerous lesions or invasive cancers were present at 4 weeks. In contrast, four mice treated with this compound exhibited little abnormalities by CT and histology. Only a minimal amount of hyperplasia was observed in one mouse.

Figure 13:
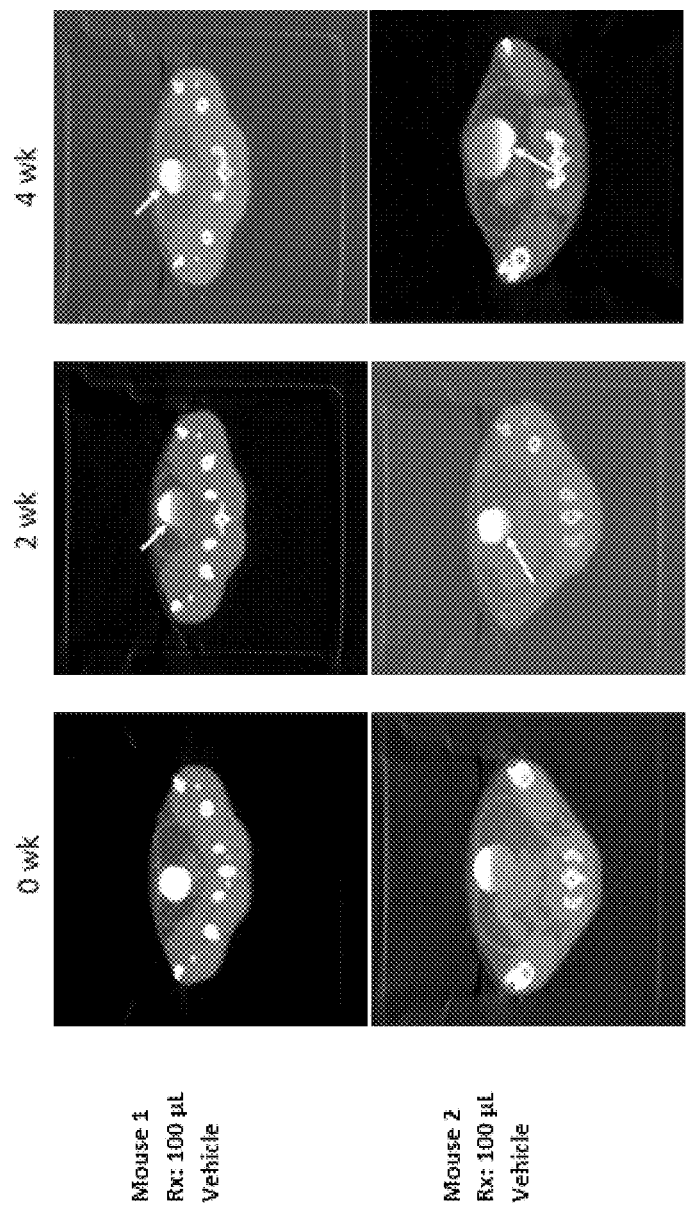
FIG. 13 provides CT urograms of a female mouse treated with vehicle control and monitored over a period of 4 weeks.

FIG. 13 shows CT urograms of a female mouse treated with vehicle control and monitored over a period of 4 weeks (top). Solid white arrows indicate bladder defects.

Figure 14:
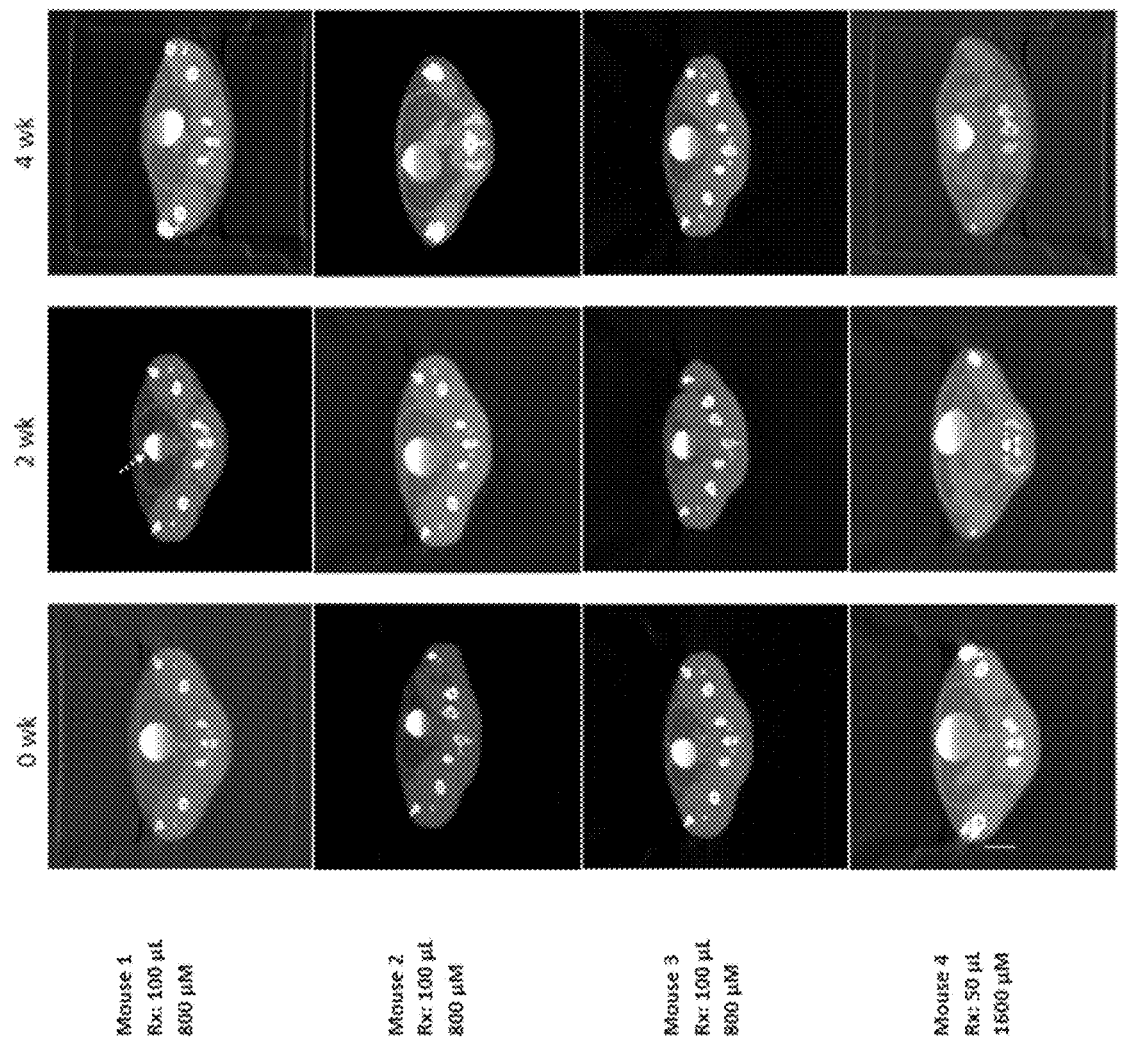
FIG. 14 provides CT urograms of a male mouse treated with compound and monitored over a period of 4 weeks.

FIG. 14 shows CT urograms of a male mouse treated with compound and monitored over a period of 4 weeks. Solid white arrows indicate bladder defects.

Figure 15:
FIG. 15 provides a histology of the bladder treated with compound and harvested after 4 weeks.

FIG. 15 shows a histology of the bladder treated with compound and harvested after 4 weeks.

In light of the foregoing, it should be appreciated that the present invention significantly advances the art by providing novel azolium salts for the treatment of bladder cancer. While particular embodiments of the invention have been disclosed in detail herein, it should be appreciated that the invention is not limited thereto or thereby inasmuch as variations on the invention herein will be readily appreciated by those of ordinary skill in the art. The scope of the invention shall be appreciated from the claims that follow.

What is claimed is:

1. A pharmaceutical composition of an antineoplastic triphenylphosphonium-substituted azolium salt for the effective treatment of human bladder cancers comprising:

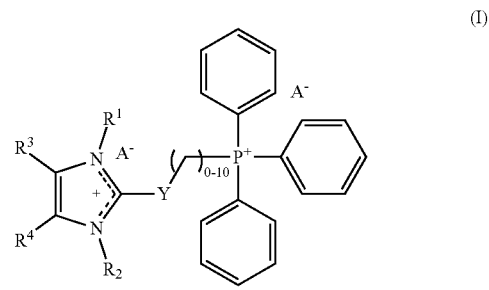

(I)

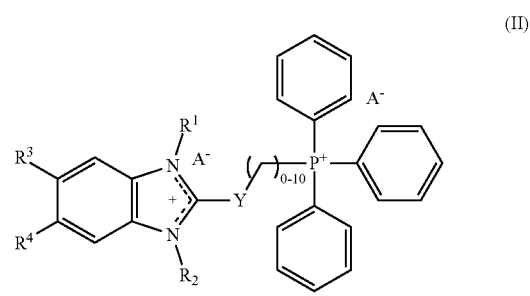

(II)

wherein, R1 and R2 are naphthalen-2-ylmethyl;

wherein, R3 and $R^4$ are each independently selected from:

hydrogen; C1 to C10 alkyl; C1 to C10 substituted alkyl; C1 to C10 alkyl heteroatom groups where the heteroatom is selected from S, O, or N; C3 to C12 cycloalkyl; C3 to C12 substituted cycloalkyl; C2 to C12 alkenyl; C3 to C12 cycloalkenyl; C3 to C12 substituted cycloalkenyl; C2 to C12 alkynyl; C6 to C12 aryl; C5 to C12 substituted aryl; polycyclic aromatics, substituted polycyclic aromatics; C6 to C12 arylalkyl; C6 to C12 alkylaryl; C3 to C12 heterocyclic; C3 to C12 substituted heterocyclic; C1 to C12 alkoxy; biphenyl; C1 to C6 alkyl biphenyl; C2 to C6 alkenyl biphenyl; or C2 to C6 alkynyl biphenyl;

wherein, A⁻ is defined as an anion independently selected as a halide, carboxylate, sulfate, phosphate, triflate, tosylate, nitrite, or borate; and wherein, Y is defined as a carbon or sulfur atom.

2. A pharmaceutical composition of an antineoplastic triphenylphosphonium-substituted azolium salt for the effective treatment of human bladder cancers comprising:

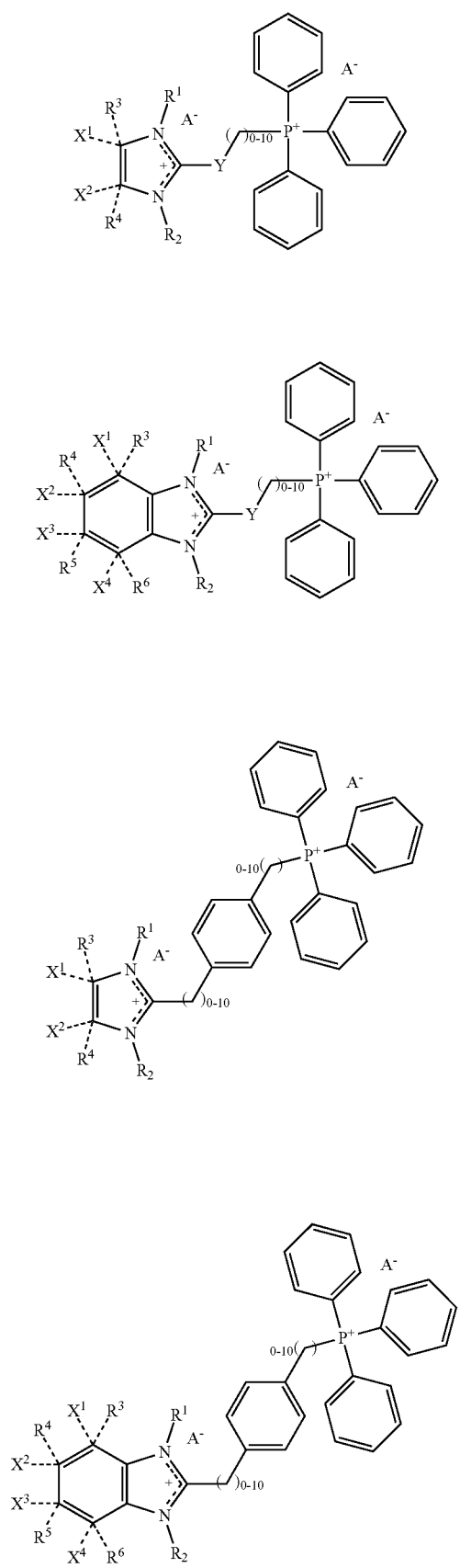
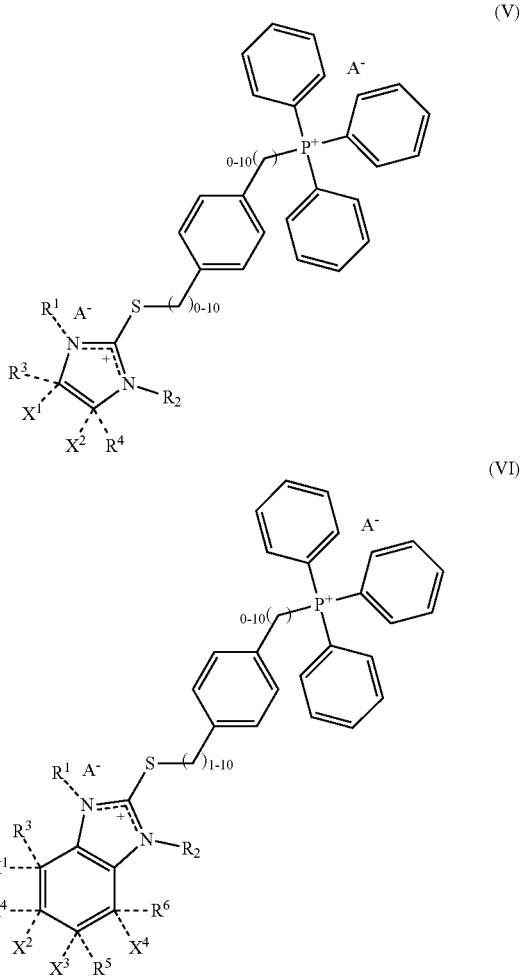

wherein, the dashed lines in the structures (I)-(VI) represent the attachment of either R or X to the corresponding ring atom;

wherein, $X^1$, $X^2$, $X^3$, $X^4$ are defined as a halogen selected from F, Cl, Br, or I, and where $X^1$, $X^2$, $X^3$, $X^4$ may be the same halogen or chosen independently;

wherein, R1 and R2 are each independently selected from:

hydrogen; C1 to C20 alkyl; C1 to C20 substituted alkyl; C1 to C20 alkyl heteroatom groups where the heterotatom is selected from S, O, or N; C3 to C12 cycloalkyl; C3 to C12 substituted cycloalkyl; C2 to C12 alkenyl; C3 to C12 cycloalkenyl; C3 to C12 substituted cycloalkenyl; C2 to C12 alkynyl; C6 to C12 aryl; C5 to C12 substituted aryl; polycyclic aromatics, substituted polycyclic aromatics; C6 to C12 arylalkyl; C6 to C12 alkylaryl; C3 to C12 heterocyclic; C3 to C12 substituted heterocyclic; C1 to C12 alkoxy; C1 to C12 alcohols; C1 to C12 carboxy; biphenyl; C1 to C6 alkyl biphenyl; C2 to C6 alkenyl biphenyl; or C2 to C6 alkynyl biphenyl;

wherein, R3, R4, R5, and R6, if present, are each independently selected from:

hydrogen; C1 to C20 alkyl; C1 to C20 substituted alkyl; C1 to C20 alkyl heteroatom groups where the heterotatom is selected from S, O, or N; C3 to C12 cycloalkyl; C3 to C12 substituted cycloalkyl; C2 to C12 alkenyl; C3 to C12 cycloalkenyl; C3 to C12 substituted cycloalkenyl; C2 to C12 alkynyl; C6 to C12 aryl; C5 to C12 substituted aryl; polycyclic aromatics, substituted polycyclic aromatics; C6 to C12 arylalkyl; C6 to C12 alkylaryl; C3 to C12 heterocyclic; C3 to C12 substituted heterocyclic; C1 to C12 alkoxy; C1 to C12 alcohols; C1 to C12 carboxy; biphenyl; C1 to C6 alkyl biphenyl; C2 to C6 alkenyl biphenyl; or C2 to C6 alkynyl biphenyl; hydroxyl; carbonyl; amino; acetyl; acetoxy; oxo; nitro; cyano; isocyano; cyanato; isocyanato;

wherein, one or more of the ring carbon atoms to which R3, R4, R5, R6 and R7 are attached can be replaced by a nitrogen, oxygen or sulfur atom;

wherein, A− is defined as an anion independently selected as a halide, hydroxide, alkoxide, aryloxide, carboxylate, sulfate, phosphate, triflate, tosylate, nitrite, or borate;

wherein, Y is defined as a carbon or sulfur atom.

* * * * *